(12) United States Patent  (10) Patent No.: US 7,776,879 B2
Buil Albero et al.  (45) Date of Patent: *Aug. 17, 2010

(54) QUINUCLIDINE CARBAMATE DERIVATIVES AND THEIR USE AS M3 ANTAGONISTS

(75) Inventors: Maria Antonia Buil Albero, Barcelona (ES); Maria Dolors Fernandez Forner, Barcelona (ES); Maria Prat Quinones, Barcelona (ES)

(73) Assignee: Almirall, S.A., Barcelona (ES)

( * ) Notice: Subject to any disclaimer, the term of this patent is extended or adjusted under 35 U.S.C. 154(b) by 270 days.

This patent is subject to a terminal disclaimer.

(21) Appl. No.: 11/806,927

(22) Filed: Jun. 5, 2007

(65) Prior Publication Data

US 2008/0021060 A1   Jan. 24, 2008

Related U.S. Application Data

(63) Continuation of application No. 10/404,395, filed on Mar. 31, 2003, now Pat. No. 7,312,231, which is a continuation of application No. 10/193,622, filed on Jul. 10, 2002, now Pat. No. 7,208,501, which is a continuation of application No. PCT/EP01/15169, filed on Dec. 20, 2001.

(51) Int. Cl.
  *A61K 31/439*  (2006.01)
  *A61P 1/00*  (2006.01)
  *A61P 11/00*  (2006.01)
  *A61P 13/00*  (2006.01)
  *C07D 453/02*  (2006.01)
(52) U.S. Cl. .................... 514/305; 546/137
(58) Field of Classification Search ............... 514/305; 546/137
  See application file for complete search history.

(56) References Cited

U.S. PATENT DOCUMENTS 2,762,796 A   9/1956   Morel et al.

(Continued)

FOREIGN PATENT DOCUMENTS

CA   1283412   4/1991

(Continued)

OTHER PUBLICATIONS

Boudinot et al., Respiratory physiology & neurobiology, (Mar. 20, 2008) vol. 161, No. 1, pp. 54-61. Electronic Publication: Dec. 5, 2007.*

(Continued)

*Primary Examiner*—D. Margaret Seaman
*Assistant Examiner*—Niloofar Rahmani
(74) *Attorney, Agent, or Firm*—Finnegan, Henderson Farabow, Garrett & Dunner LLP

(57) ABSTRACT

A carbamate of formula (I),

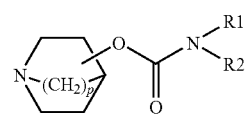

wherein R1 represents

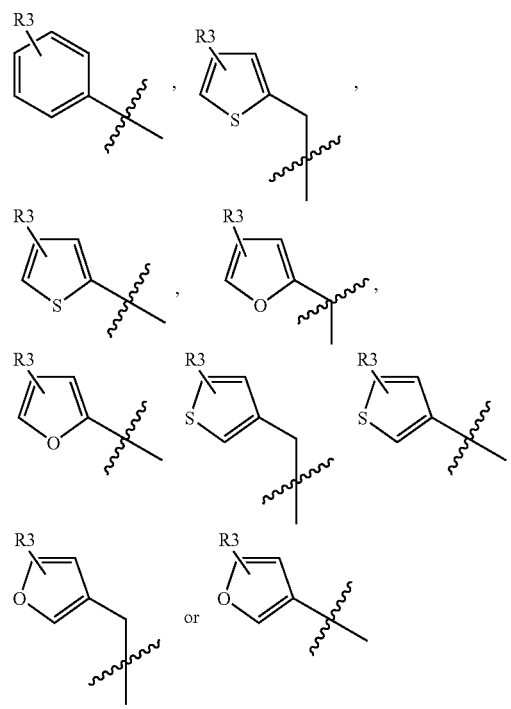

wherein R2 represents a benzyl, phenethyl, furan-2-ylmethyl, furan-3-ylmethyl, thiophen-2-ylmethyl or thiophen-3-ylmethyl group or a straight or branched alkyl group having 3 or 8 carbon atoms, an alkenyl group having 3 to 8 carbon atoms, or a cycloalkyl group of 3 to 6 carbon atoms; p is 1 or 2 and the substitution in the azoniabicylic ring may be in the 2, 3 or 4 position including all possible configurations of the asymmetric carbons; or a pharmaceutically acceptable salt thereof. The pharmaceutically acceptable salt may be of formula (II).

(II)

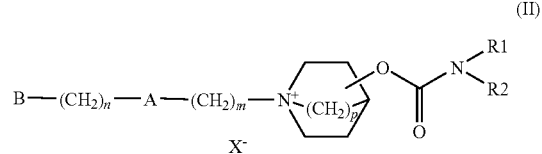

29 Claims, No Drawings

U.S. PATENT DOCUMENTS

| | | | |
|---|---|---|---|
| 3,714,357 | A | 1/1973 | Gueremy et al. |
| 5,171,744 | A | 12/1992 | Cross et al. |
| 6,916,828 | B2 | 7/2005 | Gallemi et al. |
| 7,115,629 | B2 | 10/2006 | Gallemi et al. |
| 7,208,501 | B2* | 4/2007 | Albero et al. ............... 514/305 |
| 7,312,231 | B2 | 12/2007 | Albero et al. |
| 7,435,742 | B2* | 10/2008 | Quinones et al. ............ 514/299 |
| 7,452,904 | B2* | 11/2008 | Ruiz et al. .................. 514/305 |
| 7,488,735 | B2 | 2/2009 | Quinones |
| 2004/0063950 | A1 | 4/2004 | Gallemi et al. |
| 2004/0235887 | A1 | 11/2004 | Gallemi et al. |
| 2004/0242629 | A1 | 12/2004 | Albero et al. |
| 2004/0266816 | A1 | 12/2004 | Albero et al. |
| 2005/0043349 | A1 | 2/2005 | Ruiz et al. |
| 2006/0094751 | A1 | 5/2006 | Alberto et al. |
| 2008/0021060 | A1 | 1/2008 | Albero et al. |
| 2008/0039493 | A1 | 2/2008 | Amari et al. |
| 2008/0039494 | A1 | 2/2008 | Bao et al. |
| 2009/0005412 | A1 | 1/2009 | Quinones et al. |
| 2009/0054480 | A1 | 2/2009 | Quinones et al. |
| 2009/0181935 | A1 | 7/2009 | Villetti et al. |
| 2009/0198064 | A1 | 8/2009 | Quinones |

FOREIGN PATENT DOCUMENTS

| | | |
|---|---|---|
| CA | 2155320 | 8/1993 |
| EP | 0 424 021 A1 | 4/1991 |
| EP | 0 801 067 A1 | 1/1997 |
| EP | 0 747 355 A1 | 10/1997 |
| EP | 0 863 141 A1 | 9/1998 |
| EP | 0 930 298 A1 | 7/1999 |
| FR | 2 012 964 | 3/1970 |
| FR | 2571053 | 4/1986 |
| GB | 2225574 | 6/1990 |
| GB | 1 246 606 | 7/2005 |
| JP | 09-328469 | 12/1997 |
| WO | WO 93/06098 | 4/1993 |
| WO | WO 93/16048 | 4/1993 |
| WO | WO 93/15080 | 8/1993 |
| WO | WO 01/04118 A2 | 1/2001 |
| WO | WO 01/04118 A3 | 1/2001 |
| WO | WO 02/00652 A1 | 1/2002 |
| WO | WO 02/051841 A1 | 7/2002 |
| WO | WO 02/053564 A2 | 7/2002 |
| WO | WO 03/053966 A2 | 7/2003 |
| WO | WO 2004/000840 | 12/2003 |
| WO | WO 2004/005285 | 1/2004 |
| WO | WO 2006/010452 | 2/2006 |
| WO | WO 2008/012290 | 1/2008 |
| WO | WO 2009/068253 | 6/2009 |

OTHER PUBLICATIONS

Abstract for JP 09-328469 dated Dec. 22, 1997, from Patent Abstracts of Japan.

Abstract for Wallis, R.M. & Napier, C.M. Life Sci. 64(6-7):395-401 (1996) PMID 10069502.

Abstract for White, M.V. J. Allergy Clin. Immunol. 95(5 pt 2): 1065-68 (1995) PMID 7751523.

Brown, J.H. and Taylor, P. (2001) "Muscarinic Receptor Agonists and Antagonists," Chapter 7 in The Pharmacological Basis of Therapies. Goodman et al. eds., McGraw Hill: 10th edition, pp. 155-173.

Corrected Notice of Allowance/Notice of Allowability, dated Jul. 27, 2006, from U.S. Appl. No. 10/193,622.

Eglen, R.M. and Hedge, S.S. (1997) "Muscarinic Receptor Subtypes: Pharmacology and Therapeutic Potential," Drug News Perspect. 10(8): 462-469.

Eglen, R.M. et al. "Therapeutic opportunities from muscarinic receptor research," Trends in Pharm. Sci. 22(8), Aug. 2001, 409-414.

Fryer et al., Am. J. Respir. Crit. Care Med. 158:S154-S160 (1998).

Interview Summary dated Jan. 19, 2006, from U.S. Appl. No. 10/404,395.

Interview Summary dated Jun. 13, 2006, from U.S. Appl. No. 10/193,622.

Interview Summary/Office Action dated Feb. 28, 2005, from U.S. Appl. No. 10/404,395.

Interview Summary/Office Action dated Feb. 28, 2005, in U.S. Appl. No. 10/193,622.

J. Lars et al. "Some quinuclidine derivatives with potential antimalarial activity," Acta Pharm. Suecica, vol. 5, pp. 71-76, 1968.

Konzett, H. and Rossler, R. (1940). "Versuchsanordnung zu Untersuchungen an der Brochialmuskulatur," Arch. Exp. Path. Pharmacol. 195: 71-74.

L. Noronha-Blob et al. "Stereoselective antimuscarinic effects of 3-quinuclidinyl atrolactate and 3-quinuclidinyl xanthene-9-carboxylate" European Journal of Pharmacology, vol. 221, pp. 97-103, 1992.

N.N. Godovikov, et al. "Synthesis and muscarinolytic activity of quinuclidinyl benzilate alkyl iodides" Khim. Farm. Zh., vol. 19, No. 9, pp. 1060-1061, 1985.

Notice of Allowance dated Mar. 26, 2007, from U.S. Appl. No. 10/404,395.

Notice of Allowance/Notice of Allowability, dated Jan. 19, 2006, from U.S. Appl. No. 10/404,395.

Notice of Allowance/Notice of Allowability, dated May 25, 2006, from U.S. Appl. No. 10/193,622.

Office Action dated Feb. 3, 2005, from U.S. Appl. No. 10/404,395.

Office Action dated Feb. 3, 2005, in U.S. Appl. No. 10/193,622.

Office Action dated Jul. 13, 2006, from U.S. Appl. No. 10/404,395.

Office Action dated May 18, 2005, from U.S. Appl. No. 10/404,395.

Office Action dated May 18, 2005, in U.S. Appl. No. 10/193,622.

Office Action dated Nov. 1, 2005, in U.S. Appl. No. 10/193,622.

Office Action dated Nov. 8, 2006, from U.S. Appl. No. 10/404,395.

Rang, H.P. et al. (1995). "Cholinergic Transmission," Chapter 6 in Pharmacology. Churchill Livingstone, New York, NY. 3rd Edition, pp. 117-147.

Ringdahl, R. et al. (1979). "Facile Preparation of the Enantiomers of 3-acetoxyquinuclidine and 3-quinuclidinol," Acta Pharm Suec. 16: 281-283.

S. H. Gao et al. "Stereochemistry of the Heterocyclic Alcohols Containing Piperidine Unit," Chemical Journal of Chinese Universities, vol. 20, No. 2, pp. 232-237, 1999.

Saraswati, M. et al. (1994). "Structure Activity Studies of N,N-Dialkyl and Cycloalkyl Carbamate Esters of Dimethylethanolamine and Choline with Nicotine and Muscarinic Cholinergic Properties," Drug Development Research 31: 142-146.

Shutske, G.M. (1990) "A Novel Synthesis of the Isoxazolo[5,4,3-kl]-acridine Ring System," J. Heterocyclic Chem. 27: 1617-1621.

van Zwieten et al. Cardiovascular drugs and therapy/sponsored by the International Society of Cardiovascular Pharmacotherapy, 1995, 9(1): 159-67.

Waelbroeck, M. et al. (1990). "Binding of Selective Antagonists to Four Muscarinic Receptors (M1 to M4) in Rat Forebrain," Molecular Pharmacology. 38:267-273.

Wallis, R.M. et al. "Muscarinic antagonists in the development for disorders of smooth muscle function," PMID: 10069502 (1999).

White "Muscarinic receptors in human airways," PMID: 7751523 (1995).

Xu et al. Chemical & Pharmaceutical Bulletin, 1998, 46(2): 231-241.

Abstract for JP 08-198751 dated Aug. 6, 1996, from Patent Abstracts of Japan.

Abstract for FR 2571053 dated Apr. 4, 1986, from esp@net.

Eglen, Richard M., et al., "Muscarinic receptor ligands and their therapeutic potential," Current Opinion in Chemical Biology, 3:426-432 (1999).

U.S. Appl. No. 12/205,315, filed Sep. 5, 2008, Prat Quinones et al.

U.S. Appl. No. 12/205,334, filed Sep. 5, 2008, Prat Quinones et al.

U.S. Appl. No. 10/518,714, filed Aug. 1, 2005, Prat Quinones et al.

U.S. Appl. No. 11/970,698, filed Aug. 1, 2008, Prat Quinones et al.

Abstract of Mikhlina, E.E. et al., "Synthesis and pharmacological study of 3-hydroxy- and 3-aminoquinuclidine," Khim. Farm Zhurn., 7(8): 20-24 (1973).

Abstract for Wallis, R.M. et al., "Muscarinic antagonists in development fro disorders of smooth muscle function," Life Sci. 64(6-7): 395-401 (1999).

Abstract for WO 93/16048 dated Aug. 19, 1993 from Derwent.
Atkinson et al., J. Med. Chem., vol. 20, No. 12, 1612-1617 (1977).
Fessenden et al., Organic Chemistry, 4$^{th}$ Edition, Brooks/Cole Publishing Company, p. 177 (1990).
International Search Report dated May 7, 2002 for PCT/EP 01/15169, WO 02/051841.
International Search Report dated Dec. 5, 2003 for PCT/EP2003/006472.
International Search Report dated Oct. 9, 2003 for PCT/EP2003/006708.
International Search Report dated Nov. 14, 2005 for PCT/EP2005/007424, WO 2006/010452.
Interview Summary/Office Action dated Jun. 13, 2006, from U.S. Appl. No. 10/404,395.
Interview Summary/Office Action dated May 27, 2008, in U.S. Appl. No. 10/518,496.
Langlois, M. et al. "Synthesis of (R) and (S)-3-Aminoquinuclidine from 3-Wuinuclidinone and (S) and (R)-1-Phenethylamine," Synthetic Communications, 22(13): 1895-1911 (1992).
Leonard and I. Ehrenthal, J. Am. Chem. Soc., vol. 73, 2216-2218 (1951).
Notice of Allowance/Notice of Allowability dated Jun. 9, 2008, for U.S. Appl. No. 10/518,496.
Notice of Allowance/Notice of Allowability/Interview Summary dated Oct. 6, 2008, for U.S. Appl. No. 10/518,714.
Notice of Allowance/Notice of Allowability/Interview Summary dated Dec. 31, 2009, for U.S. Appl. No. 11/970,698.
Office Action dated Jan. 22, 2010, for U.S. Appl. No. 11/658,662.
Office Action dated Oct. 5, 2009, for U.S. Appl. No. 11/658,662.
Office Action dated Nov. 21, 2007, for U.S. Appl. No. 10/518,714.
Office Action dated Feb. 28, 2008, for U.S. Appl. No. 10/518,714.
Office Action dated Dec. 7, 2007, for U.S. Appl. No. 10/518,496.
Office Action dated Sep. 22, 2009, from U.S. Appl. No. 11/970,698.
Profita et al. "Muscarinic receptors, leukotriene B4 production and neutrophilic inflammation in COPD patients," *Allergy*, 60: 1361-1369 (2005).
Sternbach et al. Journal of the American Chemical Society, 74: 2219-2221 (1952).
Reiner et al., "3-Hydroxyquinucldinium derivatives: synthesis of compounds and inhibition of acetylcholinesterase," Chemo-Biological Interactions, 119-112:173-181 (1999).

* cited by examiner

QUINUCLIDINE CARBAMATE DERIVATIVES AND THEIR USE AS M3 ANTAGONISTS

This is a continuation of application Ser. No. 10/404,395, filed on Mar. 31, 2003 now U.S. Pat. No. 7,312,231, which is a continuation of application Ser. No. 10/193,622, filed on Jul. 10, 2002; now U.S. Pat. No. 7,208,501 which is a continuation of PCT Application No. PCT EP 01/15169, filed on Dec. 20, 2001, which claims the benefit of priority from Spanish Application No. 200003084, filed on Dec. 22, 2000, all of which are incorporated herein by reference.

This invention relates to new therapeutically useful quinuclidine carbamate derivatives, to some processes for their preparation and to pharmaceutical compositions containing them.

The novel structures according to the invention are antimuscarinic agents with a potent and long lasting effect. In particular, these compounds show high affinity for muscarinic M3 receptors. This subtype of muscarinic receptor is present in glands and smooth muscle and mediates the excitatory effects of the parasympathetic system on glandular secretion and on the contraction of visceral smooth muscle (Chapter 6, Cholinergic Transmission, in H. P. Rang et al., Pharmacology, Churchill Livingstone, New York, 1995).

M3 antagonists are therefore known to be useful for treating diseases characterised by an increased parasympathetic tone, by excessive glandular secretion or by smooth muscle contraction (R. M. Eglen and S. S. Hegde, (1997), Drug News Perspect, 10(8):462-469).

Examples of this kind of diseases are respiratory disorders such as chronic obstructive pulmonary disease (COPD), bronchitis, bronchial hyperreactivity, asthma, cough and rhinitis; urological disorders such as urinary incontinence, pollakiuria, neurogenic or unstable bladder, cystospasm and chronic cystitis; gastrointestinal disorders such as irritable bowel syndrome, spastic colitis, diverticulitis and peptic ulceration; and cardiovascular disorders such as vagally induced sinus bradycardia (Chapter 7, Muscarinic Receptor Agonists and Antagonists, in Goodman and Gilman's The Pharmacological Basis of Therapeutics, 10th edition, McGraw Hill, New York, 2001).

The compounds of the invention can be used alone or in association with other drugs commonly regarded as effective in the treatment of these diseases. For example, they can be administered in combination with $\beta_2$-agonists, steroids, antiallergic drugs, phosphodiesterase IV inhibitors an/or leukotriene D4 (LTD4) antagonists for simultaneous, separate or sequential use in the treatment of a respiratory disease. The claimed compounds are useful for the treatment of the respiratory diseases detailed above in association with $\beta_2$-agonists, steroids, antiallergic drugs or phosphodiesterase IV inhibitors.

Compounds with related structures have been described as anti-spasmodics and anti-cholinergic agents in several patents.

For example, in the patent application EP 747.355 carbamate derivatives are described which are represented by the following general formula

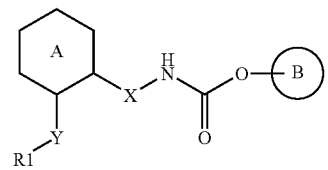

Wherein each symbol has the following meaning:

A ring is a benzene or a pyridine ring,

ring is a nitrogen-containing saturated hetero-ring which may have a substituent on the nitrogen atom and which may have a cross-linking, R1 is a phenyl group which may have a substituent, a cycloalkyl or cycloalkenyl group having 3 to 8 carbon atoms or a five- or six-membered nitrogen-containing heterocyclic group, X is a single bond or a methylene group, Y is a single bond, a carbonyl group, a methylene group which may be substituted with a hydroxyl group or a group represented by the formula —S(O)$_l$—, and l is an integer from 0-2.

These compounds clearly differ from the compounds of the present invention in terms of their structural characteristics, as they always have one hydrogen on the nitrogen of the carbamate bond.

In addition, another patent application EP 801.067 discloses compounds represented by the formula

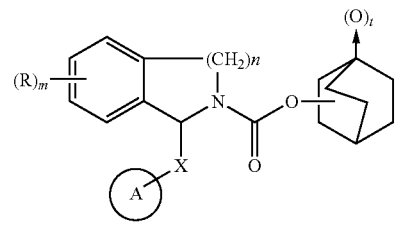

Wherein

is an aryl group, a cycloalkyl group, a cycloalkenyl group or a heteroaryl group, X is a single bond or a methylene group, l is 0 or 1, n is an integer of 1 or 2.

These compounds are also different from the compounds claimed in the present invention because the nitrogen of the carbamate group is included in a cyclic structure.

In WO 01/04118 are described compounds having the following general formula

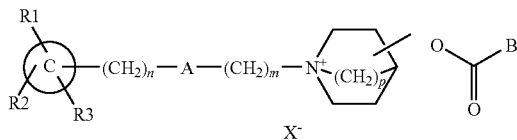

wherein B is a group of formula (i) or (ii):

i)

ii)
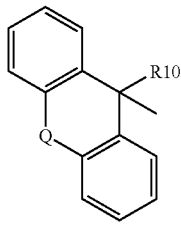

A,

R1, R2, R3, m, n, p, X⁻, Q, R8, R9 and R10 are defined in claim 1 of the cited application.

The present invention provides new compounds which are quinuclidine carbamate derivatives with potent antagonist activity at muscarinic M3 receptors and which have the chemical structure described in formula (I) or are pharmaceutically acceptable salts thereof including salts of formula (II).

Formula (I) represents a carbamate of the following general structure:

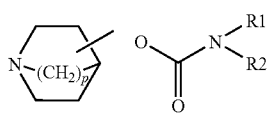

(I)

which may be quaternised to give a pharmaceutically acceptable salt of the carbamate of formula (I), in particular a salt of general formula (II)

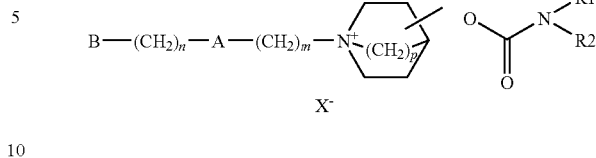

wherein:
R1 represents

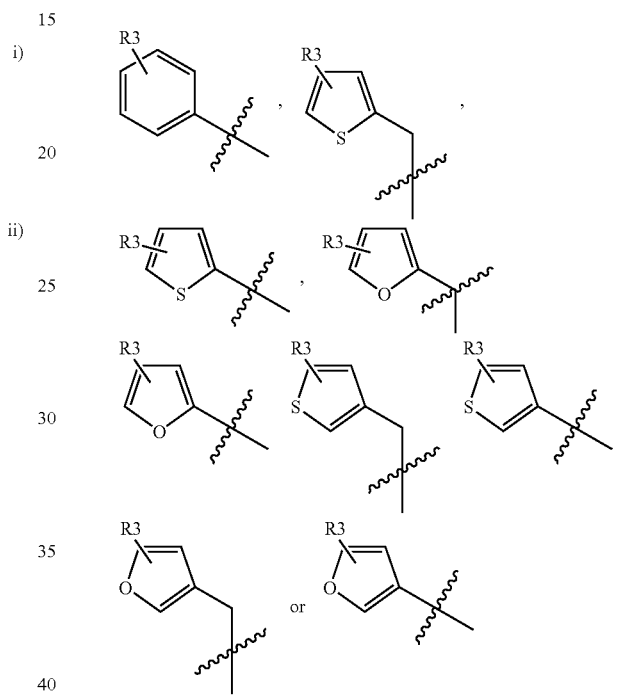

wherein R3 represents a hydrogen or halogen atom, or a straight or branched lower alkyl group or a cyano group;

R2 represents a benzyl, phenethyl, furan-2-ylmethyl, furan-3-ylmethyl, thiophen-2-ylmethyl, or thiophen-3-ylmethyl group, or a straight or branched alkyl group having 3 to 8 carbon atoms, an alkenyl group having 3 to 8 carbon atoms, or a cycloalkyl group of 3 to 6 carbon atoms;

p is 1 or 2 and the substitution in the azoniabicyclic ring may be in the 2, 3 or 4 position including all possible configurations of the asymmetric carbons;

m is an integer from 0 to 8;

A represents a —CH$_2$—, —CH=CR4-, —CR4=CH—, —CO—, —O—, —S—, —S(O), SO$_2$, —NR4-, or —CR4R5- group, wherein R4 and R5 each independently represent a hydrogen atom, a straight or branched lower alkyl group, or R4 and R5 together form an alicyclic ring;

n is an integer from 0 to 4;

B represents a hydrogen atom, an alkoxy group, a cycloalkyl group, —COOR4 or —OOCR4, wherein R4 is as defined above, or a cyano group, a naphthalenyl group, a 5,6,7,8-tetrahydronaphthalenyl group, a biphenyl group or a group of formula (I) or (ii)

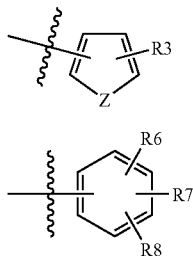

wherein Z represents O, N or S;

R3 is as defined above; and

R6, R7 and R8 each independently represent a hydrogen or halogen atom, or a hydroxy group, a phenyl group, —OR4, —SR4, —NR4R5, —NHCOR4, —CONR4R5, —CN, —NO$_2$, —COOR4 or —CF$_3$, or a straight or branched, substituted or unsubstituted lower alkyl group, wherein R4 and R5 each independently represent a hydrogen atom, a straight or branched lower alkyl group, or R4 and R5 together form an alicyclic ring; or R6 and R7 together form an aromatic, alicyclic or heterocyclic ring; and X$^-$ represents a pharmaceutically acceptable anion of a mono or polyvalent acid.

In the quaternary ammonium compounds of the present invention, including those represented by formula (II), an equivalent of an anion (X$^-$) is associated with the positive charge of the N atom. X$^-$ may be an anion of various mineral acids such as, for example, chloride, bromide, iodide, sulfate, nitrate, phosphate, or an anion of an organic acid such as, for example, acetate, trifluoroacetate, maleate, fumarate, citrate, oxalate, succinate, tartrate, malate, mandelate, methanesulfonate and p-toluenesulfonate. X$^-$ is preferably an anion selected from chloride, bromide, iodide, sulphate, nitrate, acetate, maleate, oxalate or succinate. More preferably X$^-$ is chloride, bromide, trifluoroacetate or methanesulfonate.

The lower alkyl groups and moieties mentioned herein, unless otherwise specified, are straight or branched alkyl groups containing from 1 to 6 carbon atoms, preferably from 1 to 4 carbon atoms. Preferred lower alkyl groups and moieties include methyl, ethyl, n-propyl, i-propyl, n-butyl, sec-butyl and t-butyl. Alkyl groups having 3 to 8 carbons mentioned herein, such as those present in the group R2, include n-propyl, i-propyl, n-butyl, sec-butyl, t-butyl, pentyl, hexyl, heptyl and octyl.

Optionally substituted lower alkyl groups mentioned herein include straight or branched alkyl groups containing from 1 to 6, preferably from 1 to 4, carbon atoms as mentioned above, which may be unsubstituted or substituted in any position by one or more substituents, for example by 1, 2 or 3 substituents. When two or more substituents are present, each substituent may be the same or different. The substituent(s) are typically hydroxy or alkoxy groups.

Alkenyl groups having 3 to 8 carbon atoms mentioned herein, such as those present in the group R2, are straight or branched groups such as straight or branched propenyl, butenyl, pentenyl, hexenyl, heptenyl or octenyl. The double bond may be in any position in the alkenyl group, such as on the terminal bond in relation to the carbamate group.

Alkoxy groups mentioned herein, such as those present in the group B, are typically lower alkoxy groups, that is groups containing from 1 to 6 carbon atoms, preferably from 1 to 4 carbon atoms, the hydrocarbon chain being branched or straight. Preferred alkoxy groups include methoxy, ethoxy, n-propoxy, i-propoxy, n-butoxy, sec-butoxy and t-butoxy.

Cycloalkyl groups and alicyclic groups mentioned herein, unless otherwise specified, typically contain from 3 to 8 carbon atoms, preferably from 3 to 6 carbon atoms. Cycloalkyl groups and alicyclic rings of 3 to 6 carbon atoms include cyclopropyl, cyclobutyl cyclopentyl and cyclohexyl.

The aromatic ring mentioned in relation to R6 and R7 typically contains from 5 to 14, preferably 5 to 10 carbon atoms. Examples of aromatic groups include cyclopentadienyl, phenyl and naphthalenyl.

The heterocyclic ring mentioned in relation to R6 and R7 is typically a 3 to 10 membered ring, such as a 5 or 6 membered ring, containing one or more heteroatoms selected from N, S and O. Typically, 1, 2, 3 or 4 heteroatoms are present, preferably 1 or 2 heteroatoms. Examples of heterocyclic rings include piperidyl, pyrrolidyl, azetidinyl, aziridyl, piperazinyl, morpholinyl, thiomorpholinyl, pyrrolyl, imidazolyl, imidazolidinyl, pyrazolinyl, indolinyl, isoindolinyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, quinuclidinyl, triazolyl, pyrazolyl, triazolyl, tetrazolyl and thienyl.

As used herein a halogen atom includes a fluorine, chlorine, bromine or iodine atom, typically a fluorine, chlorine or bromine atom.

The compounds of the present invention represented by formula (I) and salts thereof such as those represented by formula (II), which may have one or more asymmetric carbons, include all the possible stereoisomers. The single isomers and mixtures of the isomers fall within the scope of the present invention.

Preferred carbamates of formula (I) are those wherein R1 is a phenyl, thiophen-2-ylmethyl, thienyl or furan-2-ylmethyl group which is unsubstituted (i.e. R3 is hydrogen). If however R1 is substituted with a group R3 which is other than hydrogen, the substituent may be in the 2, 3, 4, 5 or, if R1 is a phenyl group, the 6 position. When R1 is phenyl, the substituent is preferably in the 4 position of the ring. The substituent R3 is preferably hydrogen, halogen or lower alkyl preferably hydrogen, fluorine, chlorine, methyl or ethyl and particularly preferably hydrogen, fluorine or methyl. Examples of substituted R1 groups include halo-phenyl, halo-thiophen-2-ylmethyl, halo-thienyl, halo-furan-2-ylmethyl, (C$_{1-4}$ alkyl)-phenyl, (C$_{1-4}$ alkyl)-thiophen-2-ylmethyl, (C$_{1-4}$ alkyl)-thienyl or (C$_{1-4}$ alkyl)-furan-2-ylmethyl. Specific examples include 4 fluorophenyl, 4-methylphenyl, 4-chlorophenyl, 4-ethylphenyl, 3-methylphenyl, 3-fluorophenyl, 3-chlorophenyl, 3-ethylphenyl, fluorothiophen-2-ylmethyl, fluorothienyl and fluorofuran-2-ylmethyl. Particularly preferred groups R1 include phenyl, 4-fluorophenyl, 4-methylphenyl, thiophen-2-ylmethyl, thienyl and furan 2-ylmethyl.

Preferred groups R2 include benzyl, thiophen-2-ylmethyl, thiophen-3-ylmethyl, furan-2-ylmethyl, phenethyl, pent-4-enyl, pentyl, butyl allyl or cyclopentyl.

Preferred groups —NR1R2 in formula (I) include the groups —N(benzyl)(phenyl); —N(benzyl)(4-fluorophenyl); —N(benzyl)(p-tolylphenyl); —N(butyl)(phenyl); —N(phenyl)(thiophen-2-ylmethyl); —N(phenethyl)(phenyl); —N(pentyl)(phenyl); —N(pent-4-enyl)(phenyl); —N(phenyl)(thiophen-3-ylmethyl); —N(butyl)(thiophen-2-ylmethyl); —Nbisthiophen-2-ylmethyl; —N(furan-2-ylmethyl)(thiophen-2-ylmethyl); —N(allyl)(thiophen-2-ylmethyl); —N(cyclopentyl)(thiophen-2-ylmethyl); —N(furan-2-ylmethyl)(phenyl) and —Nbisfuran-2-ylmethyl.

p is preferably 2. The substitution in the azoniabicyclo[2.2.2]octane is preferably in the 3 position. The substituted carbon atom may have (R) or (S) configuration, preferably (R) configuration.

The following compounds of general formula (I) are intended to illustrate but not to limit the scope of the present invention.

Benzylphenylcarbamic acid 1-azabicyclo[2.2.2]oct-3-(R)yl ester

Benzyl(4-fluorophenyl)carbamic acid 1-azabicyclo[2.2.2]oct-3-(R)yl ester

Benzyl-p-tolylcarbamic acid 1-azabicyclo[2.2.2]oct-3-(R)yl ester

Butylphenylcarbamic acid 1-azabicyclo[2.2.2]oct-3-(R)yl ester

Phenylthiophen-2-ylmethylcarbamic acid 1-azabicyclo[2.2.2]oct-3-(R)yl ester

Phenethylphenylcarbamic acid 1-azabicyclo[2.2.2]oct-3-(R)yl ester

Pentylphenylcarbamic acid 1-azabicyclo[2.2.2]oct-3-(R)yl ester

Pent-4-enylphenylcarbamic acid 1-azabicyclo[2.2.2]oct-3-(R)yl ester

Phenylthiophen-3-ylmethylcarbamic acid 1-azabicyclo[2.2.2]oct-3-(R)yl ester

Butylthiophen-2-ylmethylcarbamic acid 1-azabicyclo[2.2.2]oct-3-(R)yl ester

Bis-thiophen-2-ylmethylcarbamic acid 1-azabicyclo[2.2.2]oct-3-(R)yl ester

Furan-2-ylmethyl-2-thiophen-2-ylmethylcarbamic acid 1-azabicyclo[2.2.2]oct-3-(R)yl ester Allylthiophen-2-ylmethylcarbamic acid 1-azabicyclo[2.2.2]oct-3-(R)yl ester Cyclopentylthiophen-2-ylmethylcarbamic acid 1-azabicyclo[2.2.2]oct-3-(R)yl ester Furan-2-ylmethylphenylcarbamic acid 1-azabicyclo[2.2.2]oct-3-(R)yl ester Bis-furan-2-ylmethylcarbamic acid 1-azabicyclo[2.2.2]oct-3-(R)yl ester Benzylphenylcarbamic acid 1-azabicyclo[2.2.1]heptyl ester Benzylphenylcarbamic acid 1-azabicyclo[2.2.2]oct-4-yl ester and pharmaceutically acceptable salts thereof.

Preferred salts of formula (II) are those having the preferred definitions of R1, R2, —NR1R2 and p as for formula (I) above and the same location and configuration of the substituent on the azoniabicyclic ring.

Further, it is preferred that B represents a hydrogen atom or a substituted or unsubstituted phenyl, pyrrolyl, thienyl or furyl group, or a biphenyl, naphthalenyl, 5,6,7,8-tetrahydronaphthalenyl or benzo[1,3]dioxolyl group, in particular a substituted or unsubstituted phenyl or thienyl group, such as a 2-thienyl group or a 3-thienyl group, particularly a 2-thienyl group.

The thienyl, pyrrolyl or furyl group may be unsubstituted or substituted with a group R3 as defined above. The substituent may be in the 2, 3, 4 or 5 position on the ring.

The phenyl group may be unsubstituted or substituted with one, two or three groups (R6 to R8) which may be in any position on the ring. Typically it is unsubstituted or substituted with one group, for example in the 2, 3 or 4 position. Preferably, the substituents R6, R7 and R8 each independently represent a hydrogen or halogen atom, or a hydroxyl, methyl, tert-butyl, —CH$_2$OH, 3-hydroxypropyl, —OMe, —NMe$_2$, —NHCOMe, —CONH$_2$, —CN, —NO$_2$, —COOMe, or —CF$_3$ group, or R6 and R7 together form a 5- or 6-membered ring such as a phenyl or thiazolyl ring. More preferably, R6, R7 and R8 represent a hydrogen or halogen atom, or a hydroxyl, methyl, —CH$_2$OH, —OMe, —NMe$_2$, —NHCOMe, —CONH$_2$, —CN, —NO$_2$, —COOMe, or —CF$_3$ group, especially a hydrogen atom, a hydroxy group or a halogen atom, wherein the halogen atom is preferably fluorine. Examples of substituted phenyl groups which may represent B are tolyl including o-, m- and p-tolyl, 3-cyanophenyl, 2-, 3- and 4-hydroxyphenyl, 2-, 3- and 4-fluorophenyl and benzothiazolyl. B is particularly preferably a phenyl, 4-fluorophenyl or 3-hydroxyphenyl group.

Typically, n=0 or 1; m is an integer from 1 to 6, particularly 1, 2 or 3; and A represents a —CH$_2$—, —CH=CH—, —CO—, —NMe-, —O— or —S— group, in particular a —CH$_2$—, —H=CH—, or —O— group. Examples of suitable groups —(CH$_2$)$_m$-A-(CH$_2$)$_n$— include methylene, ethylene, allylene, n-propylene, i-propylene, butylene, 4-methyl pent-3-enylene, heptylene, ethyleneoxy, propyleneoxy, butyleneoxy, sulfanoylpropylene, methylaminopropylene and 4-oxobutylene, preferably methylene, ethylene, allylene, n-propylene, heptylene, ethyleneoxy or propyleneoxy.

More preferred salts of formula (II) are those wherein the azoniabicyclo group is substituted on the nitrogen atom with a 3-phenoxypropyl, 2-phenoxyethyl, 3-phenylallyl, phenethyl, 4-phenylbutyl, 3-phenylpropyl, 3-[2-hydroxyphenoxy]propyl, 3-[4-fluorophenoxy]propyl, 2-benzyloxyethyl, 3-pyrrol-1-ylpropyl, 2-thien-2-ylethyl, 3-thien-2-ylpropyl, 3-phenylaminopropyl, 3-(methylphenylamino)propyl, 3-phenylsulfanylpropyl, 3-o-tolyloxypropyl, 3-(2,4,6-trimethylphenoxy)propyl, 3-(2-tert-butyl-6-methylphenoxy)propyl, 3-(biphenyl-4-yloxy)propyl, 3-(5,6,7,8-tetrahydronaphthalen-2-yloxy)-propyl, 3-(naphthalen-2-yloxy)propyl, 3-naphthalen-1-yloxy)propyl, 3-(2-chlorophenoxy)propyl, 3-(2,4-difluorophenoxy)propyl, 3-(3-trifluoromethyl phenoxy)propyl, 3-(3-cyanophenoxy)propyl, 3-(4-cyanophenoxy)propyl, 3-(3-methoxyphenoxy)propyl, 3-(4-methoxyphenoxy)propyl, 3-benzo[1,3]dioxol-5-yloxy)propyl, 3-(2-carbamoylphenoxy)propyl, 3-(3-dimethylaminophenoxy)propyl, 3-(4-nitrophenoxy)propyl, 3-(3-nitrophenoxy)propyl, 3-(4-acetylaminophenoxy)propyl, 3-(3-methoxycarbonylphenoxy)propyl, 3-[4-(3-hydroxypropyl)phenoxy]propyl, 3-(2-hydroxymethylphenoxy)propyl, 3-(3-hydroxymethylphenoxy)propyl, 3-(4-hydroxymethylphenoxy)propyl, 3-(2-hydroxyphenoxy)propyl, 3-(4-hydroxyphenoxy)propyl, 3-(3-hydroxyphenoxy)propyl, 4-oxo-4-thien-2-ylbutyl, 3-(1-methyl-[1H]-imidazol-2-ylsulfanyl)propyl, 3-benzothiazol-2-yloxy)propyl, 3-benzyloxypropyl, 6-(4-phenylbutoxy)hexyl, 4-phenoxybutyl or 2-benzyloxyethyl group. Especially preferred salts are those wherein the azoniabicyclo group is substituted on the nitrogen atom with a 3-phenoxypropyl, 2-phenoxyethyl, 3-phenylallyl, phenethyl 3-phenylpropyl, 3-(3-hydroxyphenoxy)propyl, 3-(4-fluorophenoxy)propyl, 3-thiophen-2-ylpropyl, 1-allyl or 1-heptyl group.

The following salts of general formula (II) are intended to illustrate but not to limit the scope of the present invention.

3-(R)(Benzylphenylcarbamoyloxy)-1,3-phenylallyl)-1-azoniabicyclo[2.2.2]octane; bromide 1-Allyl-3-(R)(benzylphenylcarbamoyloxy)-1-azoniabicyclo[2.2.2]octane; bromide 3-(R)(Benzylphenylcarbamoyloxy)-1-phenethyl-1-azoniabicyclo[2.2.2]octane; bromide 3-(R)(Benzylphenylcarbamoyloxy)-1-(3-thiophen-2-yl-propyl)-1-azoniabicyclo[2.2.2]octane; bromide 3-(R)(Benzylphenylcarbamoyloxy)-1-(3-phenylpropyl)-1-azoniabicyclo[2.2.2]octane; bromide 3-(R)(Benzylphenylcarbamoyloxy)-1-(2-phenoxyethyl)-1-azoniabicyclo[2.2.2]octane; bromide 3-(R)(Butylphenylcarbamoyloxy)-1-(3-phenylallyl)-1-azoniabicyclo[2.2.2]octane; bromide 1-Allyl-3-(R)(butylphenylcarbamoyloxy)-1-azoniabicyclo[2.2.2]octane; bromide 3-(R)(Butylphenylcarbamoyloxy)-1-(2-phenoxyethyl)-1-azoniabicyclo[2.2.2]octane; bromide 3-(R)(Butylphenylcarbamoyloxy)-1-[3-(3-hydroxyphenoxy)propyl]-1-azoniabicyclo[2.2.2]octane; bromide 3-(R)(Butylphenylcarbamoyloxy)-1-[3-(4-fluorophenoxy)propyl]-1-azoniabicyclo[2.2.2]octane; bromide 3-R)(Butylphenylcarbamoyloxy)-1-(3-thiophen-2-ylpropyl)-1-azoniabicyclo[2.2.2]octane; bromide 3-(R)(Butylphenylcaxbamoyloxy)-1-(3-phenylpropyl)-1-azoniabicyclo[2.2.2]octane; bromide 3-(R)(Phenylthiophen-2-ylmethylcarbamoyloxy)-1-(3-thiophen-2-ylpropyl)-1-azonia bicyclo[2.2.2]octane; bromide 1-(2-Phenoxy-ethyl)-3-(R)-(phenyl-thiophen-2-ylmethylcarbamoyloxy)-1-azoniabicyclo[2.2.2]octane; bromide 1-Allyl-3-(R)(phenylthiophen-2-ylmethylcarbamoyloxy)-1-azoniabicyclo[2.2.2]octane; bromide 3-(R)(Phenethylphenylcarbamoyloxy)-1-(2-phenoxyethyl)-1-azoniabicyclo[2.2.2]octane; trifluoroacetate 1-Heptyl-3-(R)(pent-4-enylphenylcarbamoyloxy)-1-azoniabicyclo[2.2.2]octane; trifluoroacetate 1-Allyl-3-(R)-(phenyl-thiophen-3-ylmethyl-carbamoyloxy)-1-azonia-bicyclo[2.2.2]octane; trifluoroacetate 3-(R)phenylthiophen-3-ylmethylcarbamoyloxy)-1-(3-thiophen-2-ylpropyl)-1-azonia bicyclo[2.2.2]octane; bromide 1-(2-Phenoxyethyl)-3-(R)(phenylthiophen-3-ylmethylcarbamoyloxy)-1-azoniabicyclo[2.2.2]octane; bromide 3-(R)(Bis-thiophen-2-ylmethylcarbamoyloxy)-1-(3-phenylpropyl)-1-azoniabicyclo[2.2.2]octane; bromide 3-(R)(Bis-thiophen-2-ylmethylcarbamoyloxy)-1-(3-thiophen-2-ylpropyl)-1-azoniabicyclo[2.2.2]octane; bromide 1-Allyl-3-(R)(allylthiophen-2-ylmethylcarbamoyloxy)-1-azoniabicyclo[2.2.2]octane; trifluoroacetate 3-(R)(Cyclopentylthiophen-2-ylmethylcarbamoyloxy)-1-(3-phenylpropyl)-1-azonia bicyclo[2.2.2]octane; trifluoroacetate 3-(R)(Furan-2-ylmethylphenylcarbamoyloxy)-1-(3-phenylpropyl)-1-azoniabicyclo[2.2.2]octane; trifluoroacetate 1-Allyl-3-(R)(bis-furan-2-ylmethylcarbamoyloxy)-1-azoniabicyclo[2.2.2]octane; trifluoroacetate The present invention also provides processes for preparing compounds of formulas (I) and (II).

Compounds of general formula (I) may be prepared by method (a) illustrated in the following scheme and detailed in the experimental section.

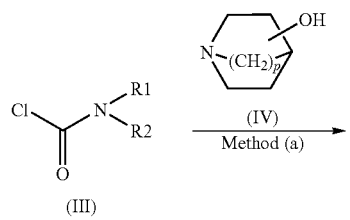

(III)

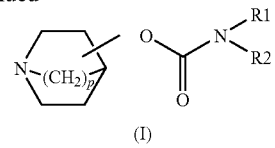

(I)

Compounds of general formula (III) may be prepared from the corresponding secondary amines following the standard method (b) described in literature.

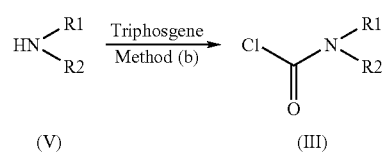

Amines of general formula (V) that are not commercially available have been prepared by synthesis according to standard methods. For example, amines wherein R1 is thiophen-2-ylmethyl and R2 is as defined above, were obtained by reductive alkylation. The corresponding aldehyde is treated with the corresponding primary amine to form the imine, which is reduced with sodium borohydride to obtain the secondary amine.

The carbamates of formula (I) may be converted to pharmaceutically acceptable salts by methods known in the art. Typically, a carbamate of formula (I) is treated with an inorganic or organic acid such as fumaric, tartaric, succinic or hydrochloric acid.

The quaternary ammonium derivatives of general formula (II), may be prepared by reaction of an alkylating agent of general formula (VI) with compounds of general formula (I). In formulas (I), (II) and (VI), R1, R2, A, B, X, n, m and p are as defined above.

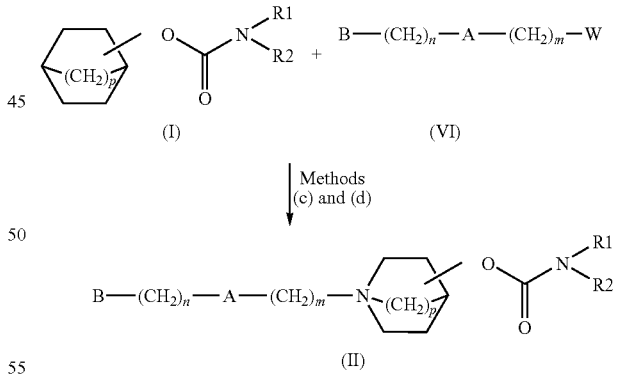

In formula (VI), W represents any suitable leaving group, such as a group X as defined above. Preferably, W represents a group X.

This alkylation reaction may be carried out by two different experimental procedures, (c) and (d) which are described below. In particular method (d) provides a new experimental process, using solid phase extraction methodologies that allows the parallel preparation of several compounds. If W represents a group other than X, the quaternary ammonium salt of formula (I) is produced from the product of method (c)

or (d) by carrying out an exchange reaction according to standard methods to replace the anion W⁻ with the desired anion X⁻.

Methods (c) and (d) are described in the experimental section. Compounds of general formula (VI) which are not commercially available have been prepared by synthesis according to standard methods. For example, compounds wherein n=0 and A=—O—, —S— or —NR4, wherein R4 is as defined above, were obtained by reaction of the corresponding aromatic derivative or its potassium salt with an alkylating agent of general formula Y—(CH₂)$_m$—X, wherein X may be a halogen and Y may be a halogen or a sulphonate ester. In other examples, compounds of general formula (VI), where n>=1 were synthesised from the corresponding alcohol derivative of general formula (VII) by known methods.

(VII)

Compounds of formula (IV) could be:
4-hydroxy-1-azabicyclo[2.2.1]heptane, described in WO93/15080
4-hydroxy-1-azabicyclo[2.2.2]octane, described in Grob, C. A. et. al. Helv. Chim. Acta (1958), 41, 1184-1190
3(R)-hydroxy-1-azabicyclo[2.2.2]octane or 3(S)-hydroxy-1-azabicyclo[2.2.2]octane, described in Ringdahl, R. Acta Pharm Suec. (1979), 16, 281-283 and commercially available from CU Chemie Uetikon GmbH.

The structures of the prepared compounds were confirmed by ¹H-NMR and MS. The NMR were recorded using a Varian 300 MHz instrument and chemical shifts are expressed as parts per million (δ) from the internal reference tetramethyl silane. Their purity was determined by HPLC, using reverse phase chromatrography on a Waters instrument, with values greater than 95% being obtained. Molecular ions were obtained by electrospray ionization mass spectrometry on a Hewlett Packard instrument. HPLC-MS experiments were performed on a Gilson instrument equipped with a binary pump (Gilson piston pump 321); a vacuum degasser (Gilson 864); an injector-fraction collector (Gilson liquid handler 215); two injection modules, analytical and preparative (Gilson 819); a valve (Gilson Valvemate 7000); a ¹/₁₀₀₀ splitter (Acurate by LC Packings); a make-up pump (Gilson 307); a diode array detector (Gilson 170) and a MS detector (a Thermoquest Finnigan aQa, a quadrupole mass spectrometer with ES an APCI ionisation modes). The HPLC-MS instrument was controlled by an IBM PC.

METHOD (a)

Example 54

Preparation of butylphenylcarbamic acid 1-azabicyclo[2.2.2]oct-3-(R)yl ester 0.65 g (28.50 mmol) of sodium was added to 70 ml of dry toluene. The suspension was refluxed with vigorous stirring. When all the sodium was melted, 3.60 g (28.30 mmol) of (R)-3-hydroxy-1-azabicyclo[2.2.2]octane was added and stirring continued for 2 hours, by which time all the sodium had reacted to form the alcoholate. 6.00 g (28.30 mmol) of Phenylbutylcarbamyl chloride dissolved in 30 ml of toluene was then slowly added. The mixture was refluxed for one hour, and then the reaction was stirred overnight at room temperature. The suspension was filtered and the filtrate evaporated. Ether was added to the residue and stirred for 10 min. The suspension was filtered and the filtrate concentrated in vacuo to obtain 7.18 g of brown oil. This product was purified by column chromatography (silica gel, chloroform/ethanol/ammonia 140:8:1) to yield 1.78 g (5.89 mmol) (22%) of a pure product, structure confirmed by ¹H-NMR. 300 MHz, CDCl3: δ 0.9 (m, 3H), 1.3 (m, 4H), 1.5 (m, 4H), 1.9 (s, 1H), 2.7 (m, 5H), 3.2 (m, 1H), 3.7 (m, 2H), 4.7 (m, 1H), 7.2-7.4 (m, 5H); MS [M+1]⁺: 303.

Example 150

Preparation of cyclopentylthiophen-2-ylmethylcarbamic acid 1-azabicyclo[2.2.2]oct-3-(R)yl ester 0.57 g (24.59 mmol) of sodium was added to 70 ml of dry toluene. The suspension was refluxed with vigorous stirring. When all the sodium was melted, 3.11 g (24.42 mmol) of (R)-3-hydroxy-1-azabicyclo[2.2.2]octane was added and stirred for 2 hours, by which time all the sodium had reacted to form the alcoholate. 4.96 g (20.35 mmol) of cyclopentylthiophen-2-ylmethylcarbamyl chloride dissolved in 30 ml of toluene was then slowly added. The mixture was refluxed for five hours, and then the reaction was stirred overnight at room temperature. The suspension was filtered and the filtrate washed with water. The organic layer was extracted with 20% HCl and the aqueous layer basified with 8N NaOH and extracted with ethyl acetate. The organic layer was washed with water, dried over Na₂SO₄ anhydride and evaporated. The oil obtained (4.50 g) was purified by column chromatography (silica gel, chloroform/ethanol/ammonia 225:8:1) to obtain 2.25 g (6.73 mmol) (33%) of a pure product, structure confirmed by ¹H-NMR. 300 MHz, (DMSO-d₆): δ 1.20-1.40 (m, 1H), 1.45-1.72 (m, 11H), 1.89 (bs, 1H), 2.45-2.62 (m, 5H), 3.03-3.10 (m, 1H), 4.22 (bs, 1H), 4.50-4.63 (m, 3H), 6.93-6.99 (m, 2H), 7.38 (m, 1H); MS [M+1]⁺: 335.

Example 159

Preparation of Benzylphenylcarbamic acid 1-azabicyclo[2.2.1]hept-4-yl ester

In a two necked flask under nitrogen, 3 ml of THF and 150 mg (1.33 mmoles) of 4-hydroxy-1-azabicyclo[2.2.1]heptane were placed. The suspension was cooled to −60° C. and 0.7 ml (1.46 mmoles) of LDA was added dropwise. After the addition the temperature was allowed to rise to 0° C. and was kept during two hours. A solution of 295 mg (1.20 mmoles) of benzylphenylcarbamyl chloride in 2 ml of THF was added in 30 minutes. The reaction mixture was allowed to slowly warm to room temperature and stirred for 18 hours. The suspension was filtered and the filtrate concentrated under reduced pressure. The residue was extracted with dichloromethane and water. The organic layer was extracted with 2N HCl and the aqueous layer basified with 8N NaOH and extracted with dichloromethane. The organic layers were dried over Na₂SO₄ anhydre and evaporated. The oil obtained (162 mg) was purified by HPLC-MS to obtain 4.86 mg (0.015 mmoles) 1.3% of a pure product as formiate, structure confirmed by ¹H-NMR 300 MHz, (DMSO-d₆): δ 1.86 (m, 4H), 2.65 (s, 2H), 2.77 (bs, 2H), 3.03 (bs, 2H), 4.84 (s, 2H), 7.14-7.32 (m, 10H). 8.19 (s, 1H); MS [M-HCOO]⁺: 323.

METHOD (b)

Carbamoyl chlorides of general formula (II) were prepared according to procedures described in the literature: M. Saraswati et al. Drug Development Research (1994), 31, 142-146; G. M. Shutske et al. J. Heterocycl. Chem. (1990), 27, 1617; GB 1246606; U.S. Pat. No. 2,762,796.

Example I-1

Preparation of Butylphenylcarbamyl Chloride

To a solution of 6.72 g (45 mmol) of butylphenylamine in 50 ml of methylene chloride cooled to 10° C. was added slowly with stirring 6.67 g (22.5 mmol) of triphosgene in 40 ml of methylene chloride. The reaction was allowed to continue at room temperature for 27 hours. The solvent was evaporated and the residue extracted twice with n-hexane. The organic solution was concentrated in vacuo to yield 9.11 g (43.03 mmol) of a yellow oil (96%). $^1$H-NMR (CDCl$_3$): δ 0.9 (m, 3H), 1.3 (m, 2H), 1.6 (m, 2H), 3.7 (m, 2H), 7.2-7.4 (m, 5H).

Example I-2

Preparation of cyclopentylthiophen-2-ylmethylcarbamyl chloride

To a solution of 5.0 g (27.58 mmol) of cyclopentylthiophen-2-ylmethylamine in 40 ml of methylene chloride at 10° C. was added slowly with stirring 4.09 g (13.79 mmol) of triphosgene in 35 ml of methylene chloride. The reaction was allowed to continue stirring at room temperature for 64 hours, refluxed for 4 hours and 25 hours more at room temperature. The solvent was evaporated and the residue extracted with n-hexane. The organic solution was concentrated to yield 4.96 g (20.34 mmol) of a brown oil (74%). $^1$H-NMR (CDCl$_3$): δ 1.4 (m, 8H), 4.2 (bs, 1H), 4.5 (m, 2H), 6.8-7.3 (m, 3H).

METHOD (c)

Example 146

Preparation of (R)-3-(bis-thiophen-2-ylmethylcarbamoyloxy)-1-(3-thiophen-2-ylpropyl)-1-azoniabicyclo[2.2.2]octane, bromide 0.54 g (1.5 mmol) of bis-thiophen-2-ylmethylcarbamic acid-1-azabicyclo[2.2.2]oct-3-(R)yl ester, 7.5 ml of tetrahydrofuran and 0.46 g (2.25 mmol) of 2-(3-bromopropyl) thiophene were mixed. The solution was refluxed for 4 hours and allowed to continue stirring at room temperature for 116 hours. Ether was added and the suspension was stirred for 30 min. The solvent was extracted and more ether was added. This procedure was repeated several times in order to eliminate the allating agent. Finally the suspension was filtered and the residue dried in the vacuum oven. The yield was 0.69 g (1.22 mmol) (81%). $^1$H-NMR (DMSO-d$_6$): 1.78-2.10 (m, 6H), 2.34 (bs, 1H), 2.82 (m, 2H), 3.21-3.46 (m, 7H), 3.89 (m, 1H), 4.54 (m, 4H), 5.06 (m, 1H), 6.95-7.01 (m, 4H), 7.07-7.11 (m, 2H), 7.38-7.49 (m, 3H); MS [M-Br]$^+$: 487; mp: 143° C.

METHOD (d)

Example 133

Preparation of 1-heptyl-3-(R)(phenylthiophen-3-ylmethylcarbamoyloxy)-1-azoniabicyclo[2.2.2]octane; trifluoroacetate 30 mg (0.08 mmols) of phenyl-thiophen-3-yl methyl carbamic acid 1-aza-bicyclo[2.2.2]oct-3-(R)yl ester were dissolved in 1 ml of DMSO. To this solution 75 mg (0.40 mmol) of heptyl bromide were added. After stirring overnight at room temperature, the mixture was purified by solid phase extraction with a cation exchange Mega Bond Elut cartridge, previously conditioned at pH=7.5 with 0.1 M NaH$_2$PO$_4$ buffer. The reaction mixture was applied to the cartridge and washed first with 2 ml of DMSO and then three times with 5 ml of CH$_3$CN, rinsing away all starting materials. The ammonium derivative was eluted with 5 ml of 0.03 M-TFA solution in CH$_3$CN:CHCl$_3$ (2:1). This solution was neutralized with 300 mg of poly(4-vinylpyridine), filtered and evaporated to dryness.

The yield was 12 mg (34%) of title compound. $^1$H-NMR (DMSO-d$_6$): δ 0.88 (m, 3H), 1.28 (m, 8H), 1.60-2.19 (m, 7H), 3.00-3.41 (m, 7H), 3.83 (m, 1H), 4.88 (s, 2H), 5.99 (m, 1H), 7.01 (m, 1H), 7.21-7.39 (m, 6H), 7.49-7.52 (m, 1H); MS [M-CF$_3$COO]$^+$: 441.

Also included within the scope of the present invention are pharmaceutical compositions which comprise, as the active ingredient, at least one quinuclidine derivative of general formula (I) or (II) in association with a pharmaceutically acceptable carrier or diluent. Preferably the composition is made up in a form suitable for oral administration.

The pharmaceutically acceptable carrier or diluents which are mixed with the active compound or compounds, to form the composition of this invention are well-known per se and the actual excipients used depend inter alia on the intended method of administration of the composition.

Compositions of this invention are preferably adapted for oral administration. In this case, the composition for oral administration may take the form of tablets, film-coated tablets, liquid inhalant, powder inhalant and inhalation aerosol; all containing one or more compounds of the invention; such preparations may be made by methods well-known in the art.

The diluents which may be used in the preparations of the compositions include those liquid and solid diluents which are compatible with the active ingredient, together with colouring or flavouring agents, if desired. Tablets or film-coated tablets may conveniently contain between 0.1 mg and 500 mg, preferably from 0.5 to 200 mg of active ingredient. The inhalant compositions may contain between 1 μg and 1,000 μg, preferably from 10 to 800 μg of active ingredient. In human therapy, the dose of the compound of general formula (I) or (II) will depend on the desired effect and duration of treatment; adult doses are generally between 0.5 mg and 300 mg per day as tablets and 10 μg and 800 μg per day as inhalant composition.

The compounds of the present invention, or pharmaceutical compositions containing them, may be used together with a β$_2$ agonist, steroid, antiallergic drug and/or phosphodiesterase IV inhibitor, for simultaneous, separate or sequential use in the treatment of a respiratory disease.

Pharmacological Action

The following examples demonstrate the excellent pharmacological activities of the compounds of the present invention. The results on human muscarinic receptor binding and in the test on bronchospasm in guinea pig, were obtained as described below.

Human Muscarinic Receptor Studies.

The binding of [$^3$H]-NMS to human muscarinic receptors was performed according to Waelbroek et al (1990), Mol. Pharmacol., 38:267-273. Assays were carried out at 25° C. Membrane preparations from stably transfected Chinese hamster ovary-K1 cells (CHO) expressing the genes for the human muscarinic M3 receptors were used.

For determination of IC$_{50}$, membrane preparations were suspended in DPBS to a final concentration of 89 μg/ml for the M3 subtype. The membrane suspension was incubated with the tritiated compound for 60 mm. After incubation the membrane fraction was separated by filtration: and the bound radioactivity determined. Non specific binding was determined by addition of $10^{-4}$ M atropine. At least six concentrations were assayed in duplicate to generate individual displacement curves.

Our results (Table 1) show that the compounds of the present invention have high affinities for muscarinic M3 receptors, preferably human muscarinic receptors.

TABLE 1

| EXAMPLE N° | BINDING TO RECPTOR M3 ($IC_{50}$ nM) |
|---|---|
| Atropine | 3.2 |
| Ipratropium | 3.0 |
| 1 | 5.0 |
| 5 | 11.1 |
| 6 | 18.0 |
| 31 | 8.0 |
| 32 | 8.0 |
| 58 | 8.0 |
| 79 | 14.0 |
| 82 | 4.5 |
| 90 | 9.2 |
| 91 | 6.8 |
| 92 | 11.5 |
| 104 | 19.0 |
| 126 | 8.6 |
| 136 | 9.0 |
| 142 | 17.8 |
| 146 | 14.4 |
| 153 | 6.0 |
| 156 | 18 |

Preferred compounds of the invention have an $IC_{50}$ (nM) value for M3 receptors of less than 35, preferably less than 25, 20 or 15, more preferably less than 10.

Test on Bronchospasm in Guinea Pig

The studies were performed according to H. Konzett and F. Rössler (1940), Arch. Exp. Path. Pharmacol. 195, 71-74. Aqueous solutions of the agents to be tested were nebulized and inhaled by anaesthetized ventilated male guinea pigs (Dunkin-Hartley). Bronchial response to intravenous acetylcholine challenge was determined before and after drug administration and changes in pulmonary resistance at several time-points were expressed as percent of inhibition of bronchospasm.

The compounds of the present invention showed bronchodilator activity with high potency and a long duration of action.

From the above described results one of ordinary skill in the art can readily understand that the compounds of the present invention have excellent antimuscarinic activity (M3) and thus are useful for the treatment of diseases in which the muscarinic M3 receptor is implicated, including respiratory diseases such as chronic obstructive pulmonary disease, bronchitis, asthma, bronchial hyperreactivity and rhinitis; urinary diseases such as urinary incontinence, pollakiuria, neurogenic bladder, nocturnal enuresis, unstable bladder, cystospasm and chronic cystitis; gastrointestinal diseases such as irritable bowel syndrome, spastic colitis, diverticulitis and peptic ulceration; and cardiovascular disorders such as vagally induced sinus bradicardia. For example, the compounds of the present invention are useful for the treatment of respiratory diseases such as chronic obstructive pulmonary disease, chronic bronchitis, asthma, and rhinitis; urinary diseases such as urinary incontinence and pollakinuria in neuripenia pollakinuria, neurogenic bladder, nocturnal enuresis, unstable bladder, cytospasm and chronic cystitis; and gastrointestinal diseases such as irritable bowel syndrome, spastic colitis and diverticulitis.

The present invention further provides a compound of formula (I) or (II) or a pharmaceutically acceptable composition comprising a compound of formula (I) or (II) for use in a method of treatment of the human or animal body by therapy, in particular for the treatment of respiratory, urinary or gastrointestinal disease.

The present invention further provides the use of a compound of formula (I) or (II) or a pharmaceutically acceptable composition comprising a compound of formula (I) or (II) for the manufacture of a medicament for the treatment of respiratory, urinary or gastrointestinal disease.

Further, the compounds of formula (I) or (II) and pharmaceutical compositions comprising a compound of formula (I) or (II) can be used in a method of treating respiratory, urinary or gastrointestinal disease, which method comprises administering to a human or animal patient in need of such treatment an effective amount of a compound of formula (I) or (II) or a pharmaceutical composition comprising a compound of formula (I) or (II).

Further, the compounds of formula (I) and pharmaceutical compositions comprising a compound of formula (I) can be used in combination with other drugs effective in the treatment of these diseases. For example with $O_2$ agonists, steroids, antiallergic drugs, phosphodiesterase IV inhibitors and/or leukotriene D4 (LTD4) inhibitors, for simultaneous, separate or sequential use in the treatment of a respiratory disease.

The present invention therefore further provides a combination product comprising (i) a compound according to the invention; and (ii) another compound effective in the treatment of a respiratory, urological or gastrointestinal disease or disorder for simultaneous, separate or sequential use.

The compound (II) which is effective in the treatment of a respiratory, urological or gastrointestinal disease or disorder may be a $\beta_2$ agonist, steroid, antiallergic drug, phosphodiesterase IV inhibitor and/or leukotriene D4 (LTD4) antagonist when the product is for simultaneous, separate or sequential use in the treatment of a respiratory disease. Alternatively, the compound (II) may be a $\beta_2$ agonist, steroid, antialergic drug and/or phosphodiesterase IV inhibitor when the product is for simultaneous, separate or sequential use in the treatment of a respiratory disease.

The present invention will be further illustrated by the following examples. The examples are given by way of illustration only and are not to be construed as limiting.

Example 1

Benzylphenylcarbamic acid 1-azabicyclo[2.2.2]oct-3-(R)yl ester

The title compound was synthesised according to method a. The yield of the final step was 1000 mg, 18%. $^1$H-NMR (CDCl$_3$): δ 1.3-1.7 (m, 4H), 1.9 (s, 1H), 2.5-2.8 (m, 5H), 3.2 (m, 1H), 4.8 (m, 1H), 4.9 (s, 2H), 7.1-7.4 (m, 10H); MS [M+1]$^+$: 337.

Example 2

3-(R)(Benzylphenylcarbamoyloxy)-1-methyl-1-azoniabicyclo[2.2.2]octane, trifluoroacetate The title compound was synthesised according to method d. The yield of the final step was 20 mg, 34%. $^1$H-NMR (DMSO-d$_6$): δ 1.54-1.90 (m, 4H), 2.17 (s, 1H), 2.95 (s, 3H), 3.22-3.52 (m, 5H), 3.84 (m, 1H), 4.92 (s, 2H), 4.99 (m, 1H), 7.12-7.37 (m, 10H); MS [M-CF$_3$COO]$^+$: 351.

Example 3

3-(R)(Benzylphenylcarbamoyloxy)-1-(4-methylpent-3-enyl)-1-azoniabicyclo[2.2.2]octane, trifluoroacetate The title compound was synthesised according to method d. The yield of the final step was 18 mg, 25%. MS [M-CF$_3$COO]$^+$: 419.

Example 4

3-(R)(Benzylphenylcarbamoyloxy)-1-(3-phenoxypropyl)-1-azoniabicyclo[2.2.2]octane; trifluoroacetate The title compound was synthesised according to method d. The yield of the final step was 21 mg, 26%. $^1$H-NMR (DMSO-d$_6$): δ 1.56-1.91 (m, 4H), 2.11-2.20 (m, 3H), 3.12 (m, 1H), 3.34-3.51 (m, 6H), 3.86 (m, 1H), 4.06 (m, 2H), 4.93 (s, 2H), 5.02 (m, 1H), 6.97 (m, 3H), 7.20-7.38 (m, 12H); MS [M-CF$_3$COO]$^+$: 471.

Example 5

3-(R)(Benzylphenylcarbamoyloxy)-1-(3-phenylallyl)-1-azoniabicyclo[2.2.2]octane; bromide The title compound was synthesised according to method c. The yield of the final step was 220 mg, 70%. $^1$H-NMR (DMSO-d$_6$): δ 1.55-1.92 (m, 4H), 2.21 (s, 1H), 3.15 (m, 1H), 3.34-3.50 (m, 5H), 3.90 (m, 1H), 4.1 (m, 2H), 4.02 (s, 2H), 5.05 (m, 1H), 6.49 (m, 1H), 6.85-6.90 (d, 1H), 7.20-7.59 (m, 12H), 7.59-7.61 (m, 2H); MS [M-Br]$^+$: 453; mp: 129° C.

Example 6

1-Allyl-3-(R)(benzylphenylcarbamoyloxy)-1-azoniabicyclo[2.2.2]octane; bromide The title compound was synthesised according to method c. The yield of the final step was 230 mg, 85%. $^1$H-NMR (DMSO-d$_6$): δ 1.58-1.91 (m, 4H), 2.20 (s, 1H), 3.10 (m, 1H), 3.27-3.41 (m, 4H), 3.79-3.90 (m, 3H), 4.92 (s, 2H), 5.03 (m, 1H), 5.61 (m, 2H), 5.98 (m, 1H), 7.20-7.38 (m, 10H); MS [M-Br]$^+$: 377; mp: 70° C.

Example 7

3-(R)(Benzylphenylcarbamoyloxy)-1-(2-hydroxyethyl)-1-azoniabicyclo[2.2.2]octane; trifluoroacetate The title compound was synthesised according to method d. The yield of the final step was 12 mg, 19%. MS [M-CF$_3$COO]$^+$: 381.

Example 8

3-(R)(Benzylphenylcarbamoyloxy)-1-isopropyl-1-azoniabicyclo[2.2.2]octane; trifluoroacetate The title compound was synthesised according to method d. The yield of the final step was 17 mg, 26%. $^1$H-NMR (DMSO-d$_6$): δ 1.24 (m, 6H), 1.64-1.89 (m, 4H), 2.20 (s, 1H), 2.78 (m, 1H), 3.23-3.32 (m, 4H), 3.50 (m, 1H), 3.76 (m, 1H), 4.92 (s, 2H), 5.06 (m, 1H), 7.20-7.38 (m, 10H); MS [M-CF$_3$COO]$^+$: 379.

Example 9

3-(R)(Benzylphenylcarbamoyloxy)-1-propyl-1-azoniabicyclo[2.2.2]octane; trifluoroacetate The title compound was synthesised according to method d. The yield of the final step was 16 mg, 25%. $^1$H-NMR (DMSO-d$_6$): δ0.88 (m, 3H), 1.57-1.68 (m, 4H), 1.89 (m, 2H), 2.18 (s, 1H), 2.99-3.14 (m, 3H), 3.26-3.40 (m, 4H), 3.83 (m, 1H), 4.92 (s, 2H), 5.01 (m, 1H), 7.20-7.37 (m, 10H); MS [M-CF$_3$COO]$^+$: 379.

Example 10

3-(R)(Benzylphenylcarbamoyloxy)-1-(3-cyanopropyl)-1-azoniabicyclo[2.2.2]octane; trifluoroacetate The title compound was synthesised according to method d. The yield of the final step was 13 mg, 19%. $^1$H-NMR (DMSO-d$_6$): δ 1.67-2.07 (m, 6H), 2.19 (s, 1H), 2.60 (m, 2H), 3.07 (m, 1H), 3.21-3.48 (m, 6H), 3.85 (m, 1H), 4.92 (s, 2H), 5.01 (m, 1H), 7.20-7.37 (m, 10); MS [M-CF$_3$COO]$^+$: 404.

Example 11

3-(R)(Benzylphenylcarbamoyloxy)-1-cyclopropylmethyl-1-azoniabicyclo[2.2.2]octane; trifluoroacetate The title compound was synthesised according to method d. The yield of the final step was 9 mg, 14%. MS [M-CF$_3$COO]$^+$: 391.

Example 12

3-(R)(Benzylphenylcarbamoyloxy)-1-(2-ethoxyethyl)-1-azoniabicyclo[2.2.2]octane; trifluoroacetate The title compound was synthesised according to method d. The yield of the final step was 22 mg, 32%. $^1$H-NMR (DMSO-d$_6$): δ 1.12 (m, 3H), 1.58-1.90 (m, 4H), 2.19 (s, 1H), 3.12-3.15 (m, 1H), 3.28-3.53 (m, 8H), 3.75 (m, 2H), 3.90 (m, 1H), 4.91 (s, 2H), 5.02 (m, 1H), 7.20-7.37 (m, 10H); MS [M-CF$_3$COO]$^+$: 409.

Example 13

3-(R)(Benzylphenylcarbamoyloxy)-1-(4-ethoxycarbonylbutyl)-1-azoniabicyclo[2.2.2]octane; trifluoroacetate The title compound was synthesised according to method d. The yield of the final step was 14 mg, 18%. $^1$H-NMR (DMSO-d$_6$): δ 1.19 (m, 3H), 1.50-1.67 (m, 4H), 1.85-1.88 (m, 2H), 2.18 (s, 1H), 2.38 (m, 2H), 3.99 (m, 1H), 3.16-3.42

(m, 8H), 3.82 (m, 1H), 4.06 (m, 2H), 4.92 (s, 2H), 5.02 (m, 1H), 7.19-7.37 (m, 10H); MS [M-CF$_3$COO]$^+$: 465.

Example 14

3-(R)(Benzylphenylcarbamoyloxy)-1-(4-phenylbutyl)-1-azoniabicyclo[2.2.2]octane; trifluoroacetate The title compound was synthesised according to method d. The yield of the final step was 14 mg, 18%. $^1$H-NMR (DMSO-d$_6$): δ 1.57-1.65 (m, 6H), 1.88 (m, 2H), 2.18 (s, 1H), 2.63 (m, 2H), 3.00 (m, 1H), 3.18-3.42 (m, 6H), 3.79-3.86 (m, 1H), 4.94 (s, 2H), 5.00 (m, 1H), 7.18-7.37 (m, 15H); MS [M-CF$_3$COO]$^+$: 469.

Example 15

3-(R)(Benzylphenylcarbamoyloxy)-1-[3-(4-fluorophenoxy)propyl]-1-azoniabicyclo[2.2.2]octane; trifluoroacetate The title compound was synthesised according to method d. The yield of the final step was 21 mg, 25%. $^1$H-NMR (DMSO-d$_6$): δ 1.55-1.91 (m, 4H), 2.10-2.20 (m, 3H), 3.10 (m, 1H), 3.28-3.50 (m, 6H), 3.88 (m, 1H), 4.02 (m, 2H), 4.93 (s, 2H), 5.02 (m, 1H), 6.95-7.12 (m, 2H), 7.12-7.38 (m, 12H); MS [M-CF$_3$COO]$^+$: 489.

Example 16

3-(R)(Benzylphenylcarbamoyloxy)-(3-hydroxypropyl)-1-azoniabicyclo[2.2.2]octane; trifluoroacetate The title compound was synthesised according to method d. The yield of the final step was 12 mg, 18%. $^1$H-NMR (DMSO-d$_6$): δ 1.54-1.88 (m, 6H), 2.18 (s, 1H), 3.09 (m, 1H), 3.23-3.49 (m, 8H), 3.85 (m, 1H), 4.84 (m, OH), 4.92 (s, 2H), 5.02 (m, 1H), 7.19-7.37 (m, 10H); MS [M-CF$_3$COO]$^+$: 395.

Example 17

1-(4-Acetoxybutyl)-3-(R)(benzylphenylcarbamoyloxy)-1-azoniabicyclo[2.2.2]octane; trifluoroacetate The title compound was synthesised according to method d. The yield of the final step was 9 mg, 12%. $^1$H-NMR (DMSO-d$_6$): δ 1.40-1.70 (m, 5H), 1.81-1.91 (m, 3H), 2.02 (m, 3H), 2.19 (s, 1H), 3.03 (m, 1H), 3.19 (m, 2H), 3.26-3.46 (m, 4H), 3.80-3.84 (m, 1H), 4.04 (m, 2H), 4.92 (s, 2H), 5.01-5.02 (m, 1H), 7.19-7.37 (m, 10H); MS [M-CF$_3$COO]$^+$: 451.

Example 18

3-(R)(Benzylphenylcarbamoyloxy-1-(4-oxo-4-thiophen-2-ylbutyl)-1-azoniabicyclo[2.2.2]octane; trifluoroacetate The title compound was synthesised according to method d. The yield of the final step was 16 mg, 19%. $^1$H-NMR (DMSO-d$_6$): δ 1.55-1.69 (m, 2H), 1.87-2.05 (m, 4H), 2.19 (s, 1H), 3.09 (m, 3H), 3.22 (m, 2H), 3.29-3.46 (m, 4H), 3.88 (m, 1H), 4.93 (s, 2H), 5.02 (m, 1H), 7.19-7.38 (m, 11H), 7.98-8.06 (m, 2H); MS [M-CF$_3$COO]$^+$: 489.

Example 19

3-(R)(Benzylphenylcarbamoyloxy)-1-[3-(3-hydroxyphenoxy)propyl]-1-azonia bicyclo[2.2.2]octane; trifluoroacetate The title compound was synthesised according to method d. The yield of the final step was 17 mg, 21%. $^1$H-NMR (DMSO-d$_6$): δ 1.57-1.68 (m, 2H), 1.90 (m, 2H), 2.08-2.19 (m, 3H), 3.11 (m, 1H), 3.28-3.50 (m, 6H), 3.88 (m, 1H), 3.97 (m, 2H), 4.93 (s, 2H), 5.02 (m, 1H), 6.33-6.40 (m, 3H), 7.04 (m, 1H), 7.20-7.38 (m, 10H), 9.5 (s, OH); MS [M-CF$_3$COO]$^+$: 487.

Example 20

3-(R)(Benzylphenylcarbamoyloxy)-1-heptyl-1-azoniabicyclo[2.2.2]octane; trifluoroacetate The title compound was synthesised according to method d. The yield of the final step was 17 mg, 23%. $^1$H-NMR (DMSO-d$_6$): δ 0.88 (m, 3H), 1.28 (m, 8H), 1.62 (m, 4H), 1.85-1.88 (m, 2H), 2.18 (s, 1H), 3.02 (m, 1H), 3.15 (m, 2H), 3.26-3.40 (m, 4H), 3.83 (m, 1H), 4.92 (s, 2H), 5.01 (m, 1H), 7.20-7.37 (m, 101H); MS [M-CF$_3$COO]$^+$: 435.

Example 21

1-(2-Benzyloxyethyl)-3-(R)(benzylphenylcarbamoyloxy)-1-azoniabicyclo[2.2.2]octane; trifluoroacetate The title compound was synthesised according to method d. The yield of the final step was 20 mg, 25%. $^1$H-NMR (DMSO-d$_6$): δ 1.54-1.94 (m, 4H), 2.20 (s, 1H), 3.17 (m, 1H), 3.28-3.55 (m, 6H), 3.85 (m, 2H), 9.92-3.99 (m, 1H), 4.53 (s, 2H), 4.91 (s, 2H), 5.02 (m, 1H), 7.18-7.40 (m, 15H); MS [M-CF$_3$COO]$^+$: 471.

Example 22

Benzyl-(4-fluorophenyl)carbamic acid 1-azabicyclo[2.2.2]oct-3-(R)yl ester

The title compound was synthesised according to method a. The yield of the final step was 1110 mg; 13%. $^1$H-NMR (DMSO-d$_6$): δ 1.16-1.52 (m, 4H), 1.81 (s, 1H), 2.42-2.57 (m, 5H), 2.99-3.07 (m, 1H), 4.63 (m, 1H), 4.84 (s, 2H), 7.10-7.32 (m, 9H); MS [M+1]: 355.

Example 23

1-Allyl-3-(R)[benzyl-(4-fluorophenyl)carbamoyloxy]-1-azoniabicyclo[2.2.2]octane; trifluoroacetate The title compound was synthesised according to method d. The yield of the final step was 10 mg, 23%. MS [M-CF$_3$COO]$^+$: 395.

Example 24

3-(R)[Benzyl-(4-fluorophenyl)carbamoyloxy]-1-(3-phenylpropyl)-1-azoniabicyclo[2.2.2]octane; trifluoroacetate The title compound was synthesised according to method d. The yield of the final step was 13 mg, 25%. MS [M-CF$_3$COO]$^+$: 473.

Example 25

Benzyl-p-tolylcarbamic acid 1-azabicyclo[2.2.2]oct-3-(R)yl ester

The title compound was synthesised according to method a. The yield of the final step was 1070 mg, 11%. $^1$H-NMR (DMSO-d$_6$): δ 1.18-1.30 (m, 2H), 1.45-1.55 (m, 2H), 1.83 (s, 1H), 2.25 (s, 3H), 2.43-2.59 (m, 5H), 3.01-3.10 (m, 1H), 4.64 (m, 1H), 4.85 (s, 2H), 7.12-7.34 (m, 9H); MS [M+1]$^+$: 351.

Example 26

1-Allyl-3-(R)(benzyl-p-tolyl-carbamoyloxy)-1-azoniabicyclo[2.2.2]octane; trifluoroacetate The title compound was synthesised according to method d. The yield of the final step was 9 mg, 19%. MS [M-CF$_3$COO]$^+$: 391.

Example 27

3-(R)(Benzyl-p-tolylcarbamoyloxy)-1-(3-phenylpropyl)-1-azoniabicyclo[2.2.2]octane; trifluoroacetate The title compound was synthesised according to method d. The yield of the final step was 13 mg, 25%. MS [M-CF$_3$COO]$^+$: 469.

Example 28

3-(R)(Benzylphenylcarbamoyloxy)-1-[2-(2-methoxyethoxy)ethyl]-1-azoniabicyclo[2.2.2]octane; bromide The title compound was synthesised according to method c. The yield of the final step was 390 mg, 84%. $^1$H-NMR (DMSO-d$_6$): δ 1.55-1.75 (m, 2H), 1.88 (m, 2H), 2.17 (s, 1H), 3.14 (m, 1H), 3.22 (s, 3H), 3.29-3.55 (m, 10H), 3.78 (m, 2H), 3.90 (m, 1H), 4.89 (s, 2H), 4.99 (m, 1H), 7.17-7.35 (m, 10H); MS [M-Br]$^+$: 439.

Example 29

3-(R)(Benzylphenylcarbamoyloxy)-1-phenethyl-1-azoniabicyclo[2.2.2]octane; bromide The title compound was synthesised according to method c. The yield of the final step was 200 mg, 65%. $^1$H-NMR (DMSO-d$_6$): δ 1.55-1.75 (m, 2H), 1.90 (m, 2H), 2.19 (s, 1H), 3.00 (m, 2H), 3.10 (m, 1H), 3.31-3.51 (m, 6H), 3.90 (m; 1H), 4.91 (s, 2H), 5.04 (m, 1H), 7.18-7.37 (m, 15H). MS [M-Br]$^+$: 441; mp 81° C.

Example 30

3-(R)(Benzylphenylcarbamoyloxy)-1-(3-thiophen-2-ylpropyl)-1-azoniabicyclo[2.2.2]octane; bromide The title compound was synthesised according to method c. The yield of the final step was 970 mg, 82%. $^1$H-NMR (DMSO-d): δ 1.55-1.69 (m, 2H), 1.85-2.04 (m, 4H), 2.18 (s, 1H), 2.83 (m, 2H), 3.01 (m, 1H), 3.20-3.44 (m, 6H), 3.85 (m, 1H), 4.92 (s, 2H), 5.00 (m, 1H), 6.94-7.00 (m, 2H), 7.19-7.40 (m, 11H). MS [M-Br]$^+$: 461; mp 95° C.

Example 31

3-(R)(Benzylphenylcarbamoyloxy)-1,3-phenylpropyl)-1-azoniabicyclo[2.2.2]octane; bromide The title compound was synthesised according to method c. The yield of the final step was 880 mg, 79%. $^1$H-NMR (DMSO-d$_6$): δ 1.55-1.69 (m, 2H), 1.85-2.00 (m, 4H), 2.18 (s, 1H), 2.59 (m, 2H), 3.04 (m, 1H), 3.23-3.44 (m, 6H), 3.85 (m, 1H), 4.92 (s, 2H), 5.02 (m, 1H), 7.18-7.36 (m, 15H).); MS [M-Br]$^+$: 455; mp 101° C.

Example 32

3-(R)(Benzylphenylcarbamoyloxy)-1-(2-phenoxyethyl)-1-azoniabicyclo[2.2.2]octane; bromide The title compound was synthesised according to method c. The yield of the final step was 360 mg, 67%. 1H-NMR (DMSO-d$_6$): δ 1.5-1.73 (m, 2H), 1.89 (m, 2H), 2.20 (s, 1H), 3.23 (m, 1H), 3.46-3.72 (m, 6H), 4.02 (m, 1H), 4.43 (m, 2H), 4.92 (s, 2H), 5.03 (m, 1H), 7.01 (m, 3H), 7.17-7.38 (m, 12H); MS [M-Br]$^+$: 457; mp 117° C.

Example 33

3-(R)(Benzylphenylcarbamoyloxy)-1-[3-(3-cyanophenoxy)propyl]-1-azoniabicyclo[2.2.2]octane; trifluoroacetate The title compound was synthesised according to method d. The yield of the final step was 16 mg, 36%; MS [M-CF$_3$COO]$^+$: 496.

Example 34

3-(R)(Benzylphenylcarbamoyloxy)-1-[3-(naphthalen-1-yloxy)propyl]-1-azoniabicyclo[2.2.2]octane; trifluoroacetate The title compound was synthesised according to method d. The yield of the final step was 10 mg, 21%; MS [M-CF$_3$COO]$^+$: 521.

Example 35

3-(R)(Benzylphenylcarbamoyloxy)-1-[3-(methylphenylamino)propyl]-1-azonia bicyclo[2.2.2]octane; trifluoroacetate The title compound was synthesised according to method d. The yield of the final step was 12 mg, 28%; MS [M-CF$_3$COO]$^+$: 484.

Example 36

3-R)(Benzylphenylcarbamoyloxy)-1-(3-phenylsulfanylpropyl-azoniabicyclo[2.2.2]octane; trifluoroacetate The title compound was synthesised according to method d. The yield of the final step was 8 mg, 18%; $^1$H-NMR (DMSO-d$_6$): δ 1.45-2.00 (m, 6H), 2.17 (bs, 1H), 3.00 (m, 2H), 3.28-3.41 (m, 7H), 3.83 (m, 1H), 4.91 (s, 2H), 4.98 (m, 1H), 7.18-7.41 (m, 15H); MS [M-CF$_3$COO]$^+$: 487.

Example 37

3-(R)(Benzylphenylcarbamoyloxy)-1-(4-oxo-4-phenylbutyl)-1-azoniabicyclo[2.2.2]octane; trifluoroacetate The title compound was synthesised according to method d. The yield of the final step was 10 mg, 23%; $^1$H-NMR (DMSO-d$_6$): δ 1.50-2.06 (m, 6H), 2.20 (bs, 1H), 3.13-3.47 (m, 9H), 3.89 (m, 1H), 4.93 (s, 2H), 5.02 (m, 1H), 7.19-7.38 (m, 10H), 7.54-7.70 (m, 3H), 7.98-8.00 (m, 2H); MS [M-CF$_3$COO]$^+$: 483.

Example 38

3-(R)(Benzylphenylcarbamoyloxy)-1-[3-(2,4,6-trimethylphenoxy)propyl]-1-azonia bicyclo[2.2.2]octane; trifluoroacetate The title compound was synthesised according to method d. The yield of the final step was 14 mg, 30%; $^1$H-NMR (DMSO-d$_6$): δ 1.50-2.20 (m, 7H), 2.19 (s, 9H), 3.16-3.52 (m, 7H), 3.73 (m, 2H), 3.92 (m, 1H), 4.93 (s, 2H), 5.03 (m, 1H), 6.83 (s, 2H), 7.19-7.38 (m, 10H); MS [M-CF$_3$COO]$^+$: 513.

Example 39

3-(R)(Benzylphenylcarbamoyloxy)-1-[3-(2-chlorophenoxy)propyl]-1-azoniabicyclo[2.2.2]octane; trifluoroacetate The title compound was synthesised according to method d. The yield of the final step was 14 mg, 31%; MS [M-CF$_3$COO]$^+$: 506.

Example 40

3-(R)(Benzylphenylcarbamoyloxy)-[3-(3-trifluoromethylphenoxy)propyl]-1-azoniabicyclo[2.2.2]octane; trifluoroacetate The title compound was synthesised according to method d. The yield of the final step was 14 mg, 29%; $^1$H-NMR (DMSO-d$_6$): δ 1.50-2.00 (m, 4H), 2.08-2.20 (m, 3H), 3.12-3.50 (m, 7H), 3.90 (m, 1H), 4.14 (m, 2H), 4.93 (s, 2H), 5.03 (m, 1H), 7.19-7.38 (m, 13H), 7.54-7.59 (m, 1H). MS [M-CF$_3$COO]$^+$: 539.

Example 41

3-(R)(Benzylphenylcarbamoyloxy)-1-[3-(biphenyl-4-yloxy)propyl]-1-azoniabicyclo[2.2.2]octane; trifluoroacetate The title compound was synthesised according to method d. The yield of the final step was 12 mg, 24%; $^1$H-NMR (DMSO-d$_6$): δ 1.50-2.20 (m, 7H), 3.14 (bs, 1H), 3.28-3.52 (m, 6H), 3.91 (m, 1H), 4.10 (m, 2H), 4.93 (s, 2H), 5.03 (m, 1H), 7.03-7.08 (m, 2H), 7.18-7.47 (m, 13H), 7.61-7.65 (m, 4H); MS [M-CF$_3$COO]$^+$: 547.

Example 42

3-(R)(Benzylphenylcarbamoyloxy)-1-[3-(2,4-difluorophenoxy)propyl]-1-azonia bicyclo[2.2.2]octane; trifluoroacetate The title compound was synthesised according to method d. The yield of the final step was 10 mg, 22%; $^1$H-NMR (DMSO-d$_6$): δ 1.50-2.19 (m, 7H), 3.10 (bs, 1H), 3.28-3.51 (m, 6H), 3.90 (m, 1H), 4.10 (m, 2H), 4.93 (s, 2H), 5.02 (m, 1H), 7.02-7.09 (m, 1H), 7.19-7.37 (m, 12H); MS [M-CF$_3$COO]$^+$: 507.

Example 43

3-(R)(Benzylphenylcarbamoyloxy)-1-[3-(4-methoxyphenoxy)propyl]-1-azonia bicyclo[2.2.2]octane; trifluoroacetate The title compound was synthesised according to method d. The yield of the final step was 10 mg, 22%; $^1$H-NMR (DMSO-d$_6$): 1.50-2.19 (m, 7H), 3.11 (bs, 1H), 3.28-3.51 (m, 6H), 3.70 (s, 3H), 3.89 (m, 1H), 3.94-3.99 (m, 2H), 4.93 (s, 2H), 5.02 (m, 1H), 6.85-6.92 (m, 4H), 7.19-7.38 (m, 10H); MS [M-CF$_3$COO]$^+$: 501.

Example 44

3-(R)(Benzylphenylcarbamoyloxy)-1-[3-(5,6,7,8-tetrahydronaphthalen-2-yloxy)propyl]-1-azoniabicyclo[2.2.2]octane; trifluoroacetate The title compound was synthesised according to method d. The yield of the final step was 10 mg, 21%; $^1$H-NMR (DMSO-d$_6$): δ 1.50-1.71 (m, 6H), 1.87-2.19 (m, 5H), 2.63-2.68 (m, 4H), 3.10 (bs, 1H), 3.28-3.50 (m, 6H), 3.88 (m, 1H), 3.98 (m, 2H), 4.93 (s, 2H), 5.02 (m, 1H), 6.63-6.70 (m, 2H), 6.95-6.98 (d, 1H), 7.19-7.38 (m, 10H); MS [M-CF$_3$COO]$^+$: 525.

Example 45

1-[3-(Benzo[1,3]dioxol-5-yloxy)propyl]-3-(R)(benzylphenylcarbamoyloxy)-1-azonia bicyclo[2.2.2] octane; trifluoroacetate The title compound was synthesised according to method d. The yield of the final step was 12 mg, 26%; MS [M-CF$_3$COO]$^+$: 515.

Example 46

3-(R)(Benzylphenylcarbamoyloxy)-1-[3-(2-carbamoylphenoxy)propyl]-1-azonia bicyclo[2.2.2]octane; trifluoroacetate The title compound was synthesised according to method d. The yield of the final step was 10 mg, 22%; $^1$H-NMR (DMSO-$d_6$): δ 1.50-2.27 (m, 7H), 3.09 (bs, 1H), 3.28-3.48 (m, 6H), 3.88 (m, 1H), 4.14 (m, 2H), 4.93 (s, 2H), 5.04 (m, 1H), 7.02-7.15 (m, 2H), 7.19-7.38 (m, 10H), 7.44-7.50 (m, 1H), 7.55 (bs, NH$_2$), 7.69-7.72 (dd, 1H); MS [M-CF$_3$COO]$^+$: 514.

Example 47

3-(R)(Benzylphenylcarbamoyloxy)-1-[3-(3-dimethylaminophenoxy)propyl]-1-azoniabicyclo[2.2.2]octane; trifluoroacetate The title compound was synthesised according to method d. The yield of the final step was 12 mg, 26%; MS [M-CF$_3$COO]$^+$: 514.

Example 48

1-[3-(4-Acetylaminophenoxy)propyl]-3-(R)(benzylphenylcarbamoyloxy)-1-azonia bicyclo[2.2.2]octane; trifluoroacetate The title compound was synthesised according to method d. The yield of the final step was 12 mg, 25%; $^1$H-NMR (DMSO-$d_6$): δ 1.50-1.92 (m, 4H), 2.01 (s, 3H), 2.04-2.20 (m, 3H), 3.12 (bs, 1H), 3.28-3.51 (m, 6H), 3.89 (m, 1H), 4.00 (m, 2H), 4.93 (s, 2H), 5.02 (m, 1H), 6.86-6.91 (m, 2H), 7.19-7.38 (m, 10H), 7.48-7.53 (m, 2H), 9.85 (s, NH); MS [M-CF$_3$COO]$^+$: 528.

Example 49

3-(R)(Benzylphenylcarbamoyloxy)-1-[3-(4-methoxycarbonylphenoxy)propyl]-1-azoniabicyclo[2.2.2]octane; trifluoroacetate The title compound was synthesised according to method d. The yield of the final step was 12 mg, 25%; $^1$H-NMR (DMSO-$d_6$): δ 1.50-2.20 (m, 7H), 3.12 (bs, 1H), 3.29-3.51 (m, 6H), 3.82 (s, 3H), 3.87-3.93 (m, 1H), 4.14 (m, 2H), 4.93 (s, 2H), 5.03 (m, 1H), 7.04-7.09 (m, 2H), 7.19-7.38 (m, 10H), 7.92-7.96 (m, 2H); MS [M-CF$_3$COO]$^+$: 529.

Example 50

3-(R)(Benzylphenylcarbamoyloxy)-1-[3-(4-nitrophenoxy)propyl]-1-azoniabicyclo[2.2.2]octane; trifluoroacetate The title compound was synthesised according to method d. The yield of the final step was 12 mg, 26%; $^1$H-NMR (DMSO-$d_6$): δ 1.50-2.27 (m, 7H), 3.12 (bs, 1H), 3.29-3.51 (m, 6H), 3.87-3.94 (m, 1H), 4.21 (m, 2H), 4.93 (s, 2H), 5.03 (m, 1H), 7.14-7.38 (m, 12H), 8.22-8.28 (m, 2H); MS [M-CF$_3$COO]$^+$: 516.

Example 51

3-(R)(Benzylphenylcarbamoyloxy)-1-[3-(4-hydroxymethylphenoxy)propyl]-1-azoniabicyclo[2.2.2]octane; trifluoroacetate The title compound was synthesised according to method d. The yield of the final step was 10 mg, 22%; MS [M-CF$_3$COO]$^+$: 501.

Example 52

Benzylphenylcarbamic acid 1-azabicyclo[2.2.2]oct-3-(S)yl ester

The title compound was synthesised according to method a. The yield of the final step was 1000 mg, 23%; $^1$H-NMR (DMSO-$d_6$): δ 1.14-1.57 (m, 4H), 1.83 (bs, 1H), 2.43-2.61 (m, 5H), 2.61-3.01 (m, 1H), 4.64 (m, 1H), 4.89 (s, 2H), 7.16-7.35 (m, 10H). MS [M+1]$^+$: 337.

Example 53

3-(S)(Benzylphenylcarbamoyloxy)-1-(3-phenylpropyl)-1-azoniabicyclo[2.2.2]octane; bromide The title compound was synthesised according to method c. The yield of the final step was 660 mg, 83%. $^1$H-NMR (DMSO-d): δ 1.40-2.00 (m, 6H), 2.18 (bs, 1H), 2.59 (m, 2H), 2.95-3.44 (m, 7H), 3.84 (m, 1H), 4.92 (s, 2H), 5.00 (m, 1H), 7.19-7.36 (m, 15H) MS [M-Br]$^+$: 455; mp: 64° C.

Example 54

Butylphenylcarbamic acid 1-azabicyclo[2.2.2]oct-3-(R)yl ester

The title compound was synthesised according to method a. The yield of the final step was 1880 mg, 22%; $^1$H-NMR (CDCl$_3$): δ 0.9 (m, 3H), 1.3 (m, 4H), 1.5 (m, 4H), 1.9 (s, 1H), 2.7 (m, 5H), 3.2 (m, 1H), 3.7 (m, 2H), 4.7 (m, 1H), 7.2-7.4 (m, 5H); MS [M+1]$^+$: 303.

Example 55

3-(R)(Butylphenylcarbamoyloxy)-1-methyl-1-azoniabicyclo[2.2.2]octane; trifluoroacetate The title compound was synthesised according to method d. The yield of the final step was 16 mg, 30%; MS [M-CF$_3$COO]$^+$: 317.

Example 56

3-(R)(Butylphenylcarbamoyloxy)-1-(4-methylpent-3-enyl)-1-azoniabicyclo[2.2.2]octane; trifluoroacetate The title compound was synthesised according to method d. The yield of the final step was 18 mg, 27%; MS [M-CF$_3$COO]$^+$: 385.

Example 57

3-(R)(Butylphenylcarbamoyloxy)-1-(3-phenoxypropyl)-1-azoniabicyclo[2.2.2]octane; trifluoroacetate The title compound was synthesised according to method d. The yield of the final step was 21 mg, 28%; MS [M-CF$_3$COO]$^+$: 437.

Example 58

3-(R)(Butylphenylcarbamoyloxy)-1-(3-phenylallyl)-1-azoniabicyclo[2.2.2]octane; bromide The title compound was synthesised according to method c. The yield of the final step was 182 mg, 48%; $^1$H-NMR (DMSO-d$_6$): δ 0.84 (m, 3H), 1.25 (m, 2H), 1.40 (m, 2H), 1.70-1.91 (m, 4H), 2.20 (s, 1H), 3.2-3.4 (m, 6H), 3.64 (m, 2H), 3.88 (m, 1H), 3.88-4.07 (d, 2H), 4.97 (m, 1H), 6.45 (m, 1H), 6.83-6.88 (d, 1H), 7.23-7.45 (m, 7H), 7.60 (m, 2H); MS [M-Br]$^+$: 419; mp: 144° C.

Example 59

1-Allyl-3-(R)(butylphenylcarbamoyloxy)-1-azoniabicyclo[2.2.2]octane; bromide

The title compound was synthesised according to method c. The yield of the final step was 200 mg, 72%; $^1$H-NMR (DMSO-d$_6$): δ 0.85 (m, 3H), 1.21-1.34 (m, 3H), 1.40-1.45 (m, 2H), 1.70-2.18 (m, 4H), 3.15-3.40 (m, 5H), 3.61-3.67 (m, 2H), 3.82 (m, 1H), 3.92-3.94 (m, 2H), 4.95 (m, 1H), 5.62 (m, 2H), 5.97-6.01 (m, 1H), 7.26-7.44 (m, 5H); MS [M-Br]$^+$: 343; mp: 141° C.

Example 60

3(R)(Butylphenylcarbamoyloxy)-1-(2-hydroxyethyl)-1-azoniabicyclo[2.2.2]octane; trifluoroacetate The title compound was synthesised according to method d. The yield of the final step was 13 mg, 19%; MS [M-CF$_3$COO]$^+$: 347.

Example 61

3-R)(Butylphenylcarbamoyloxy)-1-isopropyl-1-azoniabicyclo[2.2.2]octane; trifluoroacetate The title compound was synthesised according to method d. The yield of the final step was 20 mg, 29%; MS [M-CF$_3$COO]$^+$: 345.

Example 62

3-(R)(Butylphenylcarbamoyloxy)-1-propyl-1-azoniabicyclo[2.2.2]octane; trifluoroacetate The title compound was synthesised according to method d. The yield of the final step was 16 mg, 23%; MS [M-CF$_3$COO]$^+$: 345.

Example 63

3-(R)(Butylphenylcarbamoyloxy)-1-(3-cyanopropyl)-1-azoniabicyclo[2.2.2]octane; trifluoroacetate The title compound was synthesised according to method d. The yield of the final step was 15 mg, 20%; MS [M-CF$_3$COO]$^+$: 370.

Example 64

3-(R)(Butylphenylcarbamoyloxy)-1-cyclopropylmethyl-1-azoniabicyclo[2.2.2]octane; trifluoroacetate The title compound was synthesised according to method d. The yield of the final step was 2 mg, 3%; MS [M-CF$_3$COO]$^+$: 357.

Example 65

3-(R)(Butylphenylcarbamoyloxy)-(2-ethoxyethyl)-1-azoniabicyclo[2.2.2]octane; trifluoroacetate The title compound was synthesised according to method d. The yield of the final step was 19 mg, 25%; MS [M-CF$_3$COO]$^+$: 375.

Example 66

3-(R)(Butylphenylcarbamoyloxy)-1-(4-ethoxycarbonylbutyl)-1-azoniabicyclo[2.2.2]octane; trifluoroacetate The title compound was synthesised according to method d. The yield of the final step was 12 mg, 14%; MS [M-CF$_3$COO]$^+$: 431.

Example 67

3-(R)(Butylphenylcarbamoyloxy)-1-(3-hydroxypropyl)-1-azoniabicyclo[2.2.2]octane; trifluoroacetate The title compound was synthesised according to method d. The yield of the final step was 12 mg, 17%; MS [M-CF$_3$COO]$^+$: 361.

Example 68

3-(R)(Butylphenylcarbamoyloxy)-(3-pyrrol-1-ylpropyl)-1-azoniabicyclo[2.2.2]octane; trifluoroacetate The title compound was synthesised according to method d. The yield of the final step was 19 mg, 23%; MS [M-CF$_3$COO]$^+$: 410.

Example 69

1-(4-Acetoxybutyl)-3-(R)(butylphenylcarbamoyloxy)-1-azoniabicyclo[2.2.2]octane; trifluoroacetate The title compound was synthesised according to method d. The yield of the final step was 10 mg, 12%; MS [M-CF$_3$COO]$^+$: 417.

Example 70

3-(R)(Butylphenylcarbamoyloxy)-1-(4-oxo-4-thiophen-2-ylbutyl)-1-azoniabicyclo[2.2.2]octane; trifluoroacetate The title compound was synthesised according to method d. The yield of the final step was 17 mg, 19%; MS [M-CF$_3$COO]$^+$: 455.

Example 71

3-(R)(Butylphenylcarbamoyloxy)-1-(4-phenylbutyl)-1-azoniabicyclo[2.2.2]octane; trifluoroacetate The title compound was synthesised according to method d. The yield of the final step was 17 mg, 20%; MS [M-CF$_3$COO]$^+$: 435.

Example 72

3-(R)(Butylphenylcarbamoyloxy)-1-[3-(3-hydroxyphenoxy)propyl]-1-azoniabicyclo[2.2.2]octane; trifluoroacetate The title compound was synthesised according to method d. The yield of the final step was 21 mg, 23%; MS [M-CF$_3$COO]$^+$: 453.

Example 73

3-(R)(Butylphenylcarbamoyloxy)-1-heptyl-1-azoniabicyclo[2.2.2]octane; trifluoroacetate The title compound was synthesised according to method d. The yield of the final step was 17 mg, 21%; MS [M-CF$_3$COO]$^+$: 401.

Example 74

1-(2-Benzyloxyethyl)-3-(R)(butylphenylcarbamoyloxy)-1-azoniabicyclo[2.2.2]octane; trifluoroacetate The title compound was synthesised according to method d. The yield of the final step was 22 mg, 25%; MS [M-CF$_3$COO]$^+$: 437.

Example 75

3-(R)(Butylphenylcarbamoyloxy)-1-phenethyl-1-azoniabicyclo[2.2.2]octane; bromide The title compound was synthesised according to method c. The yield of the final step was 330 mg, 82%; $^1$H-NMR (DMSO-d$_6$): δ 0.83 (m, 3H), 1.27-1.34 (m, 2H), 1.41-1.48 (m, 3H), 1.60-2.23 (m, 4H), 2.96-3.47 (m, 7H), 3.57-3.71 (m, 4H), 3.92 (m, 1H), 4.98 (m, 1H), 7.25-7.45 (m, 10H); MS [M-Br]$^+$: 407; mp: 139° C.

Example 76

3-(R)(Butylphenylcarbamoyloxy)-1-[2-(2-methoxyethoxy)ethyl]-1-azoniabicyclo[2.2.2]octane; bromide The title compound was synthesised according to method c. The yield of the final step was 520 mg, 81%; $^1$H-NMR (DMSO-d$_6$): δ 0.82 (m, 3H), 1.24-1.31 (m, 2H), 1.39-1.47 (m, 2H), 1.70-2.20 (m, 5H), 3.26 (s, 3H), 3.35-3.70 (m, 13H), 3.82-3.86 (m, 3H), 4.94 (m, 1H), 7.26-7.44 (m, 5H); MS [M-Br]$^+$: 405.

Example 77

Butyl-(4-fluorophenyl)carbamic acid 1-azabicyclo[2.2.2]oct-3-(R)yl ester

The title compound was synthesised according to method a. The yield of the final step was 1650 mg, 24%; $^1$H-NMR (DMSO-d$_6$): δ 0.82 (m, 3H), 1.20-1.54 (m, 8H), 1.83 (m, 1H), 2.49-2.70) (m, 5H), 3.02-3.09 (m, 1H), 3.36-3.63 (m, 2H), 4.59 (m, 1H), 7.19-7.35 (m, 4H); MS [M+1]$^+$: 321.

Example 78

3-(R)(Butylphenylcarbamoyloxy)-1-[3-(4-fluorophenoxy)propyl]-1-azoniabicyclo[2.2.2]octane; chloride The title compound was synthesised according to method c. The yield of the final step was 390 mg, 75%; $^1$H-NMR (DMSO-d$_6$): δ 0.82 (m, 3H), 1.26-1.31 (m, 2H), 1.40-1.48 (m, 2H), 1.70-2.17 (m, 5H), 3.20-3.7 (m, 11H), 3.86 (m, 1H), 4.02 (m, 2H), 4.94 (m, 1H), 6.95-7.00 (m, 2H), 7.12-7.18 (m, 2H), 7.26-7.44 (m, 5H); MS [M-Cl]$^+$: 455; mp: 126° C.

Example 79

3-(R)(Butylphenylcarbamoyloxy)-1-(2-phenoxyethyl)-1-azoniabicyclo[2.2.2]octane; bromide The title compound was synthesised according to method c. The yield of the final step was 260 mg, 53%; $^1$H-NMR (DMSO-d$_6$): δ 0.84 (m, 3H), 1.23-1.30 (m, 2H), 1.39-1.48 (m, 2H), 1.70-2.20 (m, 5H), 3.20-3.72 (m, 9H), 3.99 (m, 1H), 4.44 (m, 2H), 4.95 (m, 1H), 7.01 (m, 3H), 7.24-7.40 (m, 7H); MS [M-Br]$^+$: 423; mp: 153° C.

Example 80

3-(R)(Butylphenylcarbamoyloxy)-1-(3-thiophen-2-ylpropyl)-1-azoniabicyclo[2.2.2]octane; bromide The title compound was synthesised according to method c. The yield of the final step was 1100 mg, 62%; $^1$H-NMR (DMSO-d): δ 0.84 (m, 3H), 1.24-1.31 (m, 2H), 1.42 (m, 2H), 1.60-2.21 (m, 7H), 2.85 (m, 2H), 3.0-3.50 (m, 7H), 3.60-3.69 (m, 2H), 3.85 (m, 1H), 4.93 (m, 1H), 6.95-7.00 (m, 2H), 7.28-7.43 (m, 6H); MS [M-Br]$^+$: 427; mp: 127° C.

Example 81

3-(R)(Butylphenylcarbamoyloxy)-1-(3-phenylpropyl)-1-azoniabicyclo[2.2.2]octane; bromide The title compound was synthesised according to method c. The yield of the final step was 280 mg, 56%; $^1$H-NMR (DMSO-d$_6$): δ 0.84 (m, 3H), 1.23-1.33 (m, 2H), 1.43 (m, 2H), 1.60-2.20 (m, 7H), 2.59 (m, 2H), 3.00-3.78 (m, 9H), 3.84 (m, 1H), 4.92 (m, 1H), 7.20-7.42 (m, 10H); MS [M-Br]$^+$: 421; mp: 120° C.

Example 82

Phenylthiophen-2-ylmethylcarbamic acid 1-azabicyclo[2.2.2]oct-3-(R)yl ester

The title compound was synthesised according to method a. The yield of the final step was 310 mg, 10%; $^1$H-NMR (DMSO-d$_6$): δ 1.10-1.60 (m, 4H), 1.87 (s, 1H), 2.46-2.63 (m, 5H), 3.04-3.33 (m, 1H), 4.66 (m, 1H), 5.01 (s, 2H), 6.87-6.94 (m, 2H), 7.20-7.43 (m, 6H); MS [M+1]$^+$: 343.

Example 83

1-Methyl-3-(R)(phenylthiophen-2-ylmethylcarbamoyloxy)-1-azoniabicyclo[2.2.2]octane; bromide The title compound was synthesised according to method c. The yield of the final step was 160 mg, 80%; $^1$H-NMR (DMSO-d$_6$): 1.65-2.00 (m, 4H), 2.20 (s, 1H), 2.98 (s, 3H), 3.32-3.52 (m, 5H), 3.85-3.92 (m, 1H), 4.98-5.04 (m, 3H), 6.94 (m, 2H), 7.24-7.45 (m, 6H); MS [M-Br]$^+$: 357.

Example 84

1-(3-Phenoxypropyl)-3-(R)(phenylthiophen-2-ylmethylcarbamoyloxy)-1-azonia bicyclo[2.2.2]octane; trifluoroacetate The title compound was synthesised according to method d. The yield of the final step was 16 mg, 42%; MS [M-CF$_3$COO]$^+$: 477.

Example 85

1-(3-Phenylpropyl)-3-(R)(phenylthiophen-2-ylmethylcarbamoyloxy)-1-azonia bicyclo[2.2.2]octane; trifluoroacetate The title compound was synthesised according to method d. The yield of the final step was 13 mg, 35%; $^1$H-NMR (DMSO-d$_6$): δ 1.72-2.3 (m, 7H), 2.58 (m, 2H), 3.00-3.48 (m, 7H), 3.84 (m, 1H), 5.04 (m, 3H), 6.92-6.94 (m, 2H), 7.20-7.43 (m, 111H); MS [M-CF$_3$COO]$^+$: 461.

Example 86

1-(3-Phenylallyl)-3-(R)(phenylthiophen-2-ylmethylcarbamoyloxy)-1-azoniabicyclo[2.2.2]octane; trifluoroacetate The title compound was synthesised according to method d. The yield of the final step was 4 mg, 11%; MS [M-CF$_3$COO]$^+$: 459.

Example 87

1-(2-Benzyloxyethyl)-3-(R)(phenylthiophen-2-ylmethylcarbamoyloxy)-1-azonia bicyclo[2.2.2]octane; trifluoroacetate The title compound was synthesised according to method d. The yield of the final step was 14 mg, 37%; MS [M-CF$_3$COO]$^+$: 477.

Example 88

1-[3-(3-Hydroxyphenoxy)propyl]-3-(R)(phenylthiophen-2-ylmethylcarbamoyloxy)-1-azoniabicyclo[2.2.2]octane; trifluoroacetate The title compound was synthesised according to method d. The yield of the final step was 11 mg, 28%; MS [M-CF$_3$COO]$^+$: 493.

Example 89

1-Heptyl-3-(R)(phenylthiophen-2-ylmethylcarbamoyloxy)-1-azoniabicyclo[2.2.2]octane; trifluoroacetate The title compound was synthesised according to method d. The yield of the final step was 13 mg, 37%; MS [M-CF$_3$COO]$^+$: 441.

Example 90

3-(R)(phenylthiophen-2-ylmethylcarbamoyloxy)-1-(3-thiophen-2-ylpropyl-1-azoniabicyclo[2.2.2]octane; bromide The title compound was synthesised according to method c. The yield of the final step was 140 mg, 48%; $^1$H-NMR (DMSO-d$_6$): δ 1.40-2.30 (m, 7H), 2.83 (m, 2H), 3.00-3.60 (m, 7H), 3.88 (m, 1H), 5.04 (m, 3H), 6.93-6.99 (m, 4H), 7.28-7.43 (m, 7H); MS [M-Br]$^+$: 467.

Example 91

1-(2-Phenoxyethyl)-3-(R)(phenylthiophen-2-ylmethylcarbamoyloxy)-1-azonia bicyclo[2.2.2]octane; bromide The title compound was synthesised according to method c. The yield of the final step was 510 mg, 80%; $^1$H-NMR (DMSO-d$_6$): δ 1.40-2.30 (m, 5H), 3.20-3.73 (m, 7H), 4.05 (m, 1H), 4.44 (bs, 2H), 5.04 (m, 3H), 6.91-7.04 (m, 5H), 7.24-7.41 (m, 8H); MS [M-Br]$^+$: 463; mp: 33° C.

Example 92

1-Ally-3-(R)(phenylthiophen-2-ylmethylcarbamoyloxy)-1-azoniabicyclo[2.2.2]octane; bromide The title compound was synthesised according to method c. The yield of the final step was 360 mg, 66%; $^1$H-NMR (DMSO-d$_6$): δ 1.40-2.30 (m, 5H), 3.00-3.41 (m, 5H), 3.81-3.92 (m, 3H), 5.04 (m, 3H), 5.61 (m, 2H), 5.93-6.05 (m, 1H), 6.93-6.96 (m, 2H), 7.24-7.46 (m, 6H); MS [M-Br]$^+$: 383; mp: 110° C.

Example 93

Phenethylphenylcarbamic acid 1-azabicyclo[2.2.2]oct-3-(R)yl ester

The title compound was synthesised according to method a. The yield of the final step was 1400 mg, 17%; $^1$H-NMR (DMSO-d$_6$): δ 1.10-1.60 (m, 4H), 1.83 (s, 1H), 2.40-2.70 (m, 5H), 2.78 (m, 2H), 3.00-3.08 (m, 1H), 3.87 (m, 2H), 4.58 (m, 1H), 7.16-7.40 (m, 10H); MS [M+1]$^+$: 351.

Example 94

1-Methyl-3-(R)(phenethylphenylcarbamoyloxy)-1-azoniabicyclo[2.2.2]octane; bromide The title compound was synthesised according to method c. The yield of the final step was 140 mg, 73%; $^1$H-NMR (DMSO-d$_6$): δ 1.40-2.30 (m, 5H), 2.80 (m, 2H), 2.94 (s, 3H), 3.10-3.50 (m, 5H), 3.78-3.95 (m, 3H), 4.89 (m, 1H), 7.16-7.41 (m, 10H); MS [M-Br]$^+$: 365; m: 203° C.

Example 95

1-Allyl-3-(R)(phenethylphenylcarbamoyloxy)-1-azoniabicyclo[2.2.2]octane; trifluoroacetate The title compound was synthesised according to method d. The yield of the final step was 11 mg, 35%; MS [M-CF$_3$COO]$^+$: 391.

Example 96

3-(R)(Phenethylphenylcarbamoyloxy)-1-(3-phenoxypropyl)-1-azoniabicyclo[2.2.2]octane; trifluoroacetate The title compound was synthesised according to method d. The yield of the final step was 16 mg, 41%; MS [M-CF$_3$COO]$^+$: 485.

Example 97

3-(R)(Phenethylphenylcarbamoyloxy)-1-(2-phenoxyethyl)-1-azoniabicyclo[2.2.2]octane; trifluoroacetate The title compound was synthesised according to method d. The yield of the final step was 15 mg, 40%; $^1$H-NMR (DMSO-d$_6$): δ 1.45-2.18 (m, 5H), 2.81 (m, 2H), 3.28-3.70 (m, 7H), 3.80-4.02 (m, 3H), 4.43 (m, 2H), 4.95 (m, 1H), 6.98-7.04 (m, 2H), 7.16-7.40 m, 13H); MS [M-CF$_3$COO]$^+$: 471.

Example 98

3-(R)(Phenethylphenylcarbamoyloxy)-1-(3-phenylpropyl)-1-azoniabicyclo[2.2.2]octane; trifluoroacetate The title compound was synthesised according to method d. The yield of the final step was 14 mg, 37%; $^1$H-NMR (DMSO-d$_6$): δ 1.45-2.20 (m, 7H), 2.59 (m, 2H); 2.81 (m, 2H), 3.05-3.5 (m, 7H), 3.78-3.89 (m, 3H), 4.91 (m, 1H), 7.17-7.42 (m, 15H); MS [M-CF$_3$COO]$^+$: 469.

Example 99

3-(R)(Phenethylphenylcarbamoyloxy)-1-(3-phenylallyl)-1-azoniabicyclo[2.2.2]octane; trifluoroacetate The title compound was synthesised according to method d. The yield of the final step was 4 mg, 11%; MS [M-CF$_3$COO]$^+$: 467.

Example 100

1-(2-Benzyloxyethyl)-3-(R)(phenethylphenylcarbamoyloxy)-1-azoniabicyclo[2.2.2]octane; trifluoroacetate The title compound was synthesised according to method d. The yield of the final step was 14 mg, 36%; MS [M-CF$_3$COO]$^+$: 485.

Example 101

1-[3-(3-Hydroxyphenoxy)propyl]-3-(R)(phenethylphenylcarbamoyloxy)-1-azonia bicyclo[2.2.2]octane; trifluoroacetate The title compound was synthesised according to method d. The yield of the final step was 14 mg, 35%; $^1$H-NMR (DMSO-d$_6$): δ 1.45-2.20 (m, 7H), 2.82 (m, 2H), 3.05-3.50 (m, 7H), 3.83-3.99 (m, 5H), 4.94 (m, 1H), 6.33-6.39 (m, 3H), 7.04-7.09 (m, 1H), 7.18-7.44 (m, 10H), 9.49 (s, OH); MS [M-CF$_3$COO]$^+$: 501.

Example 102

1-Heptyl-3-(R)(phenethylphenylcarbamoyloxy)-1-azoniabicyclo[2.2.2]octane; trifluoroacetate The title compound was synthesised according to method d. The yield of the final step was 15 mg, 42%; $^1$H-NMR (DMSO-d$_6$): δ 0.88 (m, 3H), 1.28 (m, 8H), 1.55-2.20 (m, 7H), 2.82 (m, 2H), 3.00-3.50 (m, 7H), 3.68-3.89 (m, 3H), 4.92 (m, 1H), 7.18-7.43 (m, 10H); MS [M-CF$_3$COO]$^+$: 449.

Example 103

3-(R)(Phenethylphenylcarbamoyloxy)-1-(3-thiophen-2-ylpropyl)-1-azoniabicyclo[2.2.2]octane; trifluoroacetate The title compound was synthesised according to method d. The yield of the final step was 15 mg, 39%; MS [M-CF$_3$COO]$^+$: 475.

Example 104

Pentylphenylcarbamic acid 1-azabicyclo[2.2.2]oct-3-(R)yl ester

The title compound was synthesised according to method a. The yield of the final step was 620 mg, 9%; $^1$H-NMR (DMSO-d$_6$): δ 0.83 (m, 3H), 1.22-1.30 (m, 5H), 1.43-1.56 (m, 5H), 1.83 (s, 1H), 2.42-2.65 (m, 5H), 3.01-3.06 (m, 1H), 3.59-3.65 (m, 2H), 4.49 (m, 1H), 7.22-7.41 (m, 5H); MS [M+1]$^+$: 317.

Example 105

1-Methyl-3-(R)(pentylphenylcarbamoyloxy)-1-azoniabicyclo[2.2.2]octane; bromide

The title compound was synthesised according to method c. The yield of the final step was 130 mg, 68%; $^1$H-NMR (DMSO-d$_6$): δ 0.81 (m, 3H), 1.21 (m, 5H), 1.45-2.20 (m, 6H), 2.93 (s, 3H), 3.10-3.70 (m, 7H), 3.80 (m, 1H), 4.88 (m, 1H), 7.24-7.41 (m, 5H); MS [M-Br]$^+$: 331.

Example 106

1-Allyl-3-(R)(pentylphenylcarbamoyloxy)-1-azoniabicyclo[2.2.2]octane; trifluoroacetate The title compound was synthesised according to method d. The yield of the final step was 10 mg, 35%; $^1$H-NMR (DMSO-d$_6$): δ 0.83 (m, 3H), 1.21-1.28 (m, 4H), 1.46 (m, 3H), 1.54-1.91 (m, 3H), 2.30 (m, 1H), 3.28-3.41 (m, 5H), 3.78-3.92 (m, 5H), 4.94 (m, 1H), 5.54-5.64 (m, 2H), 5.98 (m, 1H), 7.26-7.43 (m, 5H); MS [M-CF$_3$COO]$^+$: 357.

Example 107

3-(R)(Pentylphenylcarbamoyloxy)-1-(3-phenoxypropyl)-1-azoniabicyclo[2.2.2]octane; trifluoroacetate The title compound was synthesised according to method d. The yield of the final step was 13 mg, 36%; MS [M-CF$_3$COO]$^+$: 451.

Example 108

3-(R)(Pentylphenylcarbamoyloxy)-1-(2-phenoxyethyl)-1-azoniabicyclo[2.2.2]octane; trifluoroacetate The title compound was synthesised according to method d. The yield of the final step was 14 mg, 40%; $^1$H-NMR (DMSO-d$_6$): δ 0.82 (m, 3H), 1.23 (m, 4H), 1.46 (m, 3H), 1.54-1.91 (m, 3H), 2.25 (s, 1H), 3.28-3.70 (m, 9H), 3.98 (m, 1H), 4.43 (m, 2H), 4.95 (m, 1H), 6.98-7.04 (m, 3H), 7.23-7.4 (m, 7H); MS [M-CF$_3$COO]$^+$: 437.

Example 109

3-(R)(Pentylphenylcarbamoyloxy)-1-(3-phenylpropyl)-1-azoniabicyclo[2.2.2]octane; trifluoroacetate The title compound was synthesised according to method d. The yield of the final step was 13 mg, 37%; $^1$H-NMR (DMSO-d$_6$): δ 0.82 (m, 3H), 1.20-1.25 (m, 5H), 1.44 (m, 3H), 1.68-2.13 (m, 7H), 2.58 (m, 2H), 3.00-3.41 (m, 5H), 3.54-3.69 (m, 2H), 3.79-3.85 (m, 1H), 4.92 (m, 1H), 7.20-7.42 (m, 10H); MS [M-CF$_3$COO]$^+$: 435.

Example 110

3-(R)(Pentylphenylcarbamoyloxy)-1-(3-phenylallyl)-1-azoniabicyclo[2.2.2]octane; trifluoroacetate The title compound was synthesised according to method d. The yield of the final step was 4 mg, 12%; MS [M-CF$_3$COO]$^+$: 433.

Example 111

1-(2-Benzyloxyethyl)-3-(R)(pentylphenylcarbamoyloxy)-1-azoniabicyclo[2.2.2]octane; trifluoroacetate The title compound was synthesised according to method d. The yield of the final step was 15 mg, 42%; MS [M-CF$_3$COO]$^+$: 451.

Example 112

1-[3-(3-Hydroxyphenoxy)propyl]-3-(R)(pentylphenylcarbamoyloxy)-1-azonia bicyclo[2.2.2]octane; trifluoroacetate The title compound was synthesised according to method d. The yield of the final step was 12 mg, 32%; MS [M-CF$_3$COO]$^+$: 467.

Example 113

1-Heptyl-3-(R)(pentylphenylcarbamoyloxy)-1-azoniabicyclo[2.2.2]octane; trifluoroacetate The title compound was synthesised according to method d. The yield of the final step was 15 mg, 45%; MS [M-CF$_3$COO]$^+$: 415.

Example 114

3-(R)(Pentylphenylcarbamoyloxy)-1-(3-thiophen-2-ylpropyl)-1-azoniabicyclo[2.2.2]octane; trifluoroacetate The title compound was synthesised according to method d. The yield of the final step was 13 mg, 37%; $^1$H-NMR (DMSO-d$_6$): δ 0.82 (m, 3H), 1.22-1.26 (m, 5H), 1.46 (m, 3H), 1.60-2.14 (m, 7H), 2.82 (m, 2H), 3.20-3.41 (m, 5H), 3.50-3.70 (m, 2H), 3.82 (m, 1H), 4.92 (m, 1H), 6.93-6.99 (m, 2H), 7.25-7.43 (m, 6H); MS [M-CF$_3$COO]$^+$: 441.

Example 115

Pent-4-enylphenylcarbamic acid 1-azabicyclo[2.2.2]oct-3-(R)yl ester

The title compound was synthesised according to method a. The yield of the final step was 690 mg, 14%; $^1$H-NMR (DMSO-d$_6$): δ 1.10-1.60 (m, 6H), 1.84 (bs, 1H), 1.97-2.04 (m, 2H), 2.45-2.65 (m, 5H), 3.02-3.10 (m, 1H), 3.29-3.66 (m, 2H), 4.59 (m, 1H), 4.61-5.00 (m, 2H), 5.70-5.84 (m, 1H), 7.22-7.42 (m, 5H); MS [M+1]$^+$: 315.

Example 116

1-Allyl-3-(R)(pent-4-enylphenylcarbamoyloxy)-1-azoniabicyclo[2.2.2]octane; trifluoroacetate The title compound was synthesised according to method d. The yield of the final step was 10 mg, 35%; MS [M-CF$_3$COO]$^+$: 355.

Example 117

3-(R)(Pent-4-enylphenylcarbamoyloxy)-1-(3-phenoxypropyl)-1-azoniabicyclo[2.2.2]octane; trifluoroacetate The title compound was synthesised according to method d. The yield of the final step was 15 mg, 42%; $^1$H-NMR (DMSO-d$_6$): δ 1.50-2.20 (m, 11H), 3.23-3.47 (m, 7H), 3.56-3.73 (m, 2H), 3.87 (m, 1H), 4.03 (m, 2H), 4.92-4.95 (m, 2H), 5.00 (m, 1H), 5.70-5.82 (m, 1H), 6.93-6.99 (m, 2H), 7.26-7.44 (m, 8H); MS [M-CF$_3$COO]$^+$: 449.

Example 118

3-(R)(Pent-4-enylphenylcarbamoyloxy)-1-(2-phenoxyethyl)-1-azoniabicyclo[2.2.2]octane; trifluoroacetate The title compound was synthesised according to method d. The yield of the final step was 13 mg, 37%; $^1$H-NMR (DMSO-d$_6$): δ 1.55 (m, 2H), 1.65-2.20 (m, 7H), 3.28-3.75 (m, 9H), 3.98 (m, 1H), 4.43 (bs, 2H), 4.92-4.99 (m, 3H), 5.70-5.83 (m, 1H), 6.98-7.04 (m, 3H), 7.24-7.40 (m, 7H); MS [M-CF$_3$COO]$^+$: 435.

Example 119

3-(R)(Pent-4-enylphenylcarbamoyloxy)-1-(3-phenyl-propyl)-1-azoniabicyclo[2.2.2]octane; trifluoroacetate The title compound was synthesised according to method d. The yield of the final step was 13 mg, 37%; $^1$H-NMR (DMSO-$d_6$): δ 1.56 (m, 3H), 1.70-2.14 (m, 8H), 2.58 (m, 2H), 3.19-3.41 (m, 7H), 3.56-3.71 (m, 2H), 3.81 (m, 1H), 4.92-4.99 (m, 3H), 5.70-5.83 (m, 1H), 7.20-7.43 (m, 10H); MS [M-CF$_3$COO]$^+$: 433.

Example 120

3-(R)(Pent-4-enylphenylcarbamoyloxy)-1-(3-phenylallyl)-1-azoniabicyclo[2.2.2]octane; trifluoroacetate The title compound was synthesised according to method d. The yield of the final step was 4 mg, 12%; MS [M-CF$_3$COO]$^+$: 431.

Example 121

1-(2-Benzyloxyethyl)-3-(R)(pent-4-enylphenylcarbamoyloxy)-1-azoniabicyclo[2.2.2]octane; trifluoroacetate The title compound was synthesised according to method d. The yield of the final step was 16 mg, 44%; MS [M-CF$_3$COO]$^+$: 449.

Example 122

1-[3-(3-Hydroxyphenoxy)propyl]-3-(R)(pent-4-enylphenylcarbamoyloxy)-1-azonia bicyclo[2.2.2]octane; trifluoroacetate The title compound was synthesised according to method d. The yield of the final step was 12 mg, 32%; MS [M-CF$_3$COO]$^+$: 465.

Example 123

1-Heptyl-3-(R)(pent-4-enylphenylcarbamoyloxy)-1-azoniabicyclo[2.2.2]octane; trifluoroacetate The title compound was synthesised according to method d. The yield of the final step was 3 mg, 9%; MS [M-CF$_3$COO]$^+$: 413.

Example 124

1-Methyl-3-(R)(pent-4-enylphenylcarbamoyloxy)-1-azoniabicyclo[2.2.2]octane; trifluoroacetate The title compound was synthesised according to method d. The yield of the final step was 13 mg, 49%; MS [M-CF$_3$COO]$^+$: 429.

Example 125

3-(R)(Pent-4-enylphenylcarbamoyloxy)-1-(3-thiophen-2-ylpropyl)-1-azoniabicyclo[2.2.2]octane; trifluoroacetate The title compound was synthesised according to method d. The yield of the final step was 15 mg, 43%; $^1$H-NMR (DMSO-$d_6$): δ 1.40-2.20 (m, 11H), 2.82 (m, 2H), 3.05-3.5 (m, 7H), 3.58-3.86 (m, 3H), 4.92-4.95 (m, 2H) 5.00 (m, 1H), 5.70-5.84 (m, 1H), 6.93-7.00 (m, 2H), 7.26-7.44 (m, 6H); MS [M-CF$_3$COO]$^+$: 439.

Example 126

Phenylthiophen-3-ylmethylcarbamic acid 1-azabicyclo[2.2.2]oct-3-(R)yl ester

The title compound was synthesised according to method a. The yield of the final step was 2000 mg, 15%; $^1$H-NMR (DMSO-$d_6$): δ 1.10-1.60 (m, 4H), 1.84 (bs, 1H), 2.46-2.62 (m, 5H), 3.02-3.10 (m, 1H), 4.62-4.67 (m, 1H), 4.84 (s, 2H), 6.99 (m, 1H), 7.18-7.36 (m, 6H), 7.47-7.50 (m, 1H); MS [M+1]$^+$: 343.

Example 127

1-Allyl-3-(R)(phenylthiophen-3-ylmethylcarbamoyloxy)-1-azoniabicyclo[2.2.2]octane; trifluoroacetate The title compound was synthesised according to method d. The yield of the final step was 8 mg, 26%; $^1$H-NMR (DMSO-$d_6$): δ 1.45-2.00 (m, 4H), 2.21 (bs, 1H), 3.04-3.42 (m, 5H), 3.78-3.91 (m, 3H), 4.87 (s, 2H), 5.02 (m, 1H), 5.54-5.64 (m, 2H), 5.91-6.02 (m, 1H), 7.00-7.02 (m, 1H), 7.22-7.39 (m, 6H), 7.50-7.52 (m, 1H); MS [M-CF$_3$COO]$^+$: 383.

Example 128

1-(3-Phenoxypropyl)-3-(R)(phenylthiophen-3-ylmethylcarbamoyloxy)-1-azonia bicyclo[2.2.2]octane; trifluoroacetate The title compound was synthesised according to method d. The yield of the final step was 12 mg, 31%; MS [M-CF$_3$COO]$^+$: 477.

Example 129

1-(3-Phenylpropyl)-3-(R)(phenylthiophen-3-ylmethylcarbamoyloxy)-1-azonia bicyclo[2.2.2]octane; trifluoroacetate The title compound was synthesised according to method d. The yield of the final step was 15 mg, 41%; $^1$H-NMR (DMSO-$d_6$): δ 1.45-2.18 (m, 7H), 2.59 (m, 2H), 3.02-3.44 (m, 7H), 3.84 (m, 1H), 4.87 (s, 2H), 4.99 (m, 1H), 7.00 (m, 1H), 7.21-7.38 (m, 11H), 7.47-7.50 (m, 1H); MS [M-CF$_3$COO]$^+$: 461.

Example 130

1-(3-Phenylallyl)-3-(R)(phenylthiophen-3-ylmethyl-carbamoyloxy)-1-azoniabicyclo[2.2.2]octane; trifluoroacetate The title compound was synthesised according to method d. The yield of the final step was 4 mg, 11%; MS [M-CF$_3$COO]$^+$: 459.

Example 131

1-(2-Benzyloxyethyl)-3-(R)(phenylthiophen-3-ylmethylcarbamoyloxy)-1-azoniabicyclo[2.2.2]octane; trifluoroacetate The title compound was synthesised according to method d. The yield of the final step was 16 mg, 42%; MS [M-CF$_3$COO]$^+$: 477.

Example 132

1-[3-(3-Hydroxyphenoxy)propyl]-3-R)(phenylthiophen-3-ylmethylcarbamoyloxy)-1-azoniabicyclo[2.2.2]octane; trifluoroacetate The title compound was synthesised according to method d. The yield of the final step was 13 mg, 33%; MS [M-CF$_3$COO]$^+$: 493.

Example 133

1-Heptyl-3-(R)(phenylthiophen-3-ylmethylcarbamoyloxy)-1-azoniabicyclo[2.2.2]octane; trifluoroacetate The title compound was synthesised according to method d. The yield of the final step was 12 mg, 34%; $^1$H-NMR (DMSO-d$_6$): δ 0.88 (m, 3H), 1.28 (m, 8H), 1.60-2.19 (m, 7H), 3.00-3.41 (m, 7H), 3.83 (m, 1H), 4.88 (s, 2H), 5.99 (m, 1H), 7.01 (m, 1H), 7.21-7.39 (m, 6H), 7.49-7.52 (m, 1H); MS [M-CF$_3$COO]$^+$: 441.

Example 134

1-Methyl-3-(R)(phenylthiophen-3-ylmethylcarbamoyloxy)-1-azoniabicyclo[2.2.2]octane; trifluoroacetate The title compound was synthesised according to method d. The yield of the final step was 12 mg, 42%; MS [M-CF$_3$COO]$^+$: 357.

Example 135

3-(R)(Phenylthiophen-3-ylmethylcarbamoyloxy)-1,3-thiophen-2-ylpropyl)-1-azoniabicyclo[2.2.2]octane; bromide The title compound was synthesised according to method c. The yield of the final step was 500 mg, 78%; $^1$H-NMR (DMSO-d$_6$): δ 1.45-2.19 (m, 7H), 2.83 (m, 2H), 3.04-3.13 (m, 1H), 3.19-3.46 (m, 6H), 3.83-3.90 (m, 1H), 4.88 (s, 2H), 4.99 (m, 1H), 6.94 (m, 3H), 7.20-7.40 (m, 7H), 7.49 (m, 1H); MS [M-Br]$^+$: 467; mp: 110° C.

Example 136

3-(R)(Phenylthiophen-3-ylmethylcarbamoyloxy)-1-(2-phenoxyethyl)-1-azonia bicyclo[2.2.2]octane; bromide The title compound was synthesised according to method c. The yield of the final step was 350 mg, 63%; $^1$H-NMR (DMSO-d$_6$): δ 1.45-2.20 (m, 5H), 3.27 (m, 1H), 3.40-3.80 (m, 6H), 4.00-4.06 (m, 1H), 4.44 (bs, 2H), 4.87 (s, 2H), 5.02 (m, 1H), 6.99-7.04 (m, 4H), 7.20-7.38 (m, 8H), 7.48 (m, 1H); MS [M-Br]$^+$: 463; mp: 131° C.

Example 137

Butylthiophen-2-ylmethylcarbamic acid 1-azabicyclo[2.2.2]oct-3-(R)yl ester

The title compound was synthesised according to method a. The yield of the final step was 1300 mg, 29%; $^1$H-NMR (DMSO-d$_6$): δ 0.85 (m, 3H), 1.19-1.68 (m, 8H), 1.92 (m, 1H), 2.49-2.64 (m, 5H), 3.05-3.22 (m, 3H), 4.56-4.62 (m, 3H), 6.95-7.04 (m, 2H), 7.42-7.44 (m, 1H); MS [M+1]$^+$: 323.

Example 138

1-Allyl-3-(R)(butylthiophen-2-ylmethylcarbamoyloxy)-1-azoniabicyclo[2.2.2]octane; trifluoroacetate The title compound was synthesised according to method d. The yield of the final step was 10 mg, 23%; $^1$H-NMR (DMSO-d$_6$): δ 0.86 (m, 3H), 1.20-1.26 (m, 2H), 1.42-1.49 (m, 2H), 1.58-2.05 (m, 4H), 2.32 (bs, 1H), 3.20-3.41 (m, 7H), 3.74-3.94 (m, 3H), 4.51-4.72 (m, 2H), 4.99 (m, 1H), 5.55-5.64 (m, 2H), 5.87-6.10 (m, 1H), 6.99 (m, 1H), 7.08 (m, 1H), 7.46 (m, 1H); MS [M-CF$_3$COO]$^+$: 363.

Example 139

3-(R)(Butylthiophen-2-ylmethylcarbamoyloxy)-1-(3-phenylpropyl)-1-azoniabicyclo[2.2.2]octane; trifluoroacetate The title compound was synthesised according to method d. The yield of the final step was 13 mg, 25%; $^1$H-NMR (DMSO-d$_6$): δ 0.85 (m, 3H), 1.19-1.26 (m, 2H), 1.41-1.50 (m, 2H), 1.75-2.10 (m, 6H), 2.30 (bs, 1H), 2.59 (m, 2H), 3.10-3.50 (m, 9H), 3.83 (m, 1 H), 4.50-4.74 (m, 2H), 4.97 (m, 1H), 6.97 (m, 1H), 7.07 (m, 1H), 7.20-7.35 (m, 5H), 7.43 (m, 1H); MS [M-CF$_3$COO]$^+$: 441.

Example 140 bis-Thiophen-2-ylmethylcarbamic acid 1-azabicyclo[2.2.2]oct-3-(R)yl ester

The title compound was synthesised according to method a. The yield of the final step was 340 mg, 7%; $^1$H-NMR (DMSO-d$_6$): δ 1.28-1.31 (m, 1H), 1.45-1.72 (m, 3H), 1.94-1.97 (m, 1H), 2.49-2.71 (m, 5H), 3.06-3.14 (m, 1H), 4.50-4.57 (m, 4H), 4.62-4.69 (m, 1H), 6.96-7.06 (m, 4H), 7.44-7.46 (m, 2H); MS [M+1]$^+$: 363.

Example 141

1-Allyl-3-(R)(bis-thiophen-2-ylmethylcarbamoyloxy)-1-azoniabicyclo[2.2.2]octane; trifluoroacetate The title compound was synthesised according to method d. The yield of the final step was 9 mg, 19%; $^1$H-NMR (DMSO-$d_6$): δ 1.70-2.06 (m, 4H), 2.35 (bs, 1H), 3.25-3.50 (m, 5H), 3.80-3.94 (m, 3H), 4.54-4.71 (m, 4H), 5.10 (m, 1H), 5.55-5.65 (m, 2H), 5.87-6.10 (m, 1H), 6.98-7.01 (m, 2H), 7.06-7.10 (m, 2H), 7.47-7.48 (m, 2H); MS [M-CF$_3$COO]$^+$: 403.

Example 142

3-(R)(bis-thiophen-2-ylmethylcarbamoyloxy)-1-(3-phenylpropyl)-1-azoniabicyclo[2.2.2]octane; bromide The title compound was synthesised according to method c. The yield of the final step was 690 mg, 82%; $^1$H-NMR (DMSO-$d_6$): δ 1.78-2.10 (m, 6H), 2.34 (bs, 1H), 2.53-2.63 (m, 2H), 3.23-3.48 (m, 7H), 3.88 (m, 1H), 4.53-4.74 (m, 4H), 5.05 (m, 1H), 6.98-7.01 (m, 2H), 7.02-7.11 (m, 2H), 7.21-7.37 (m, 5H), 7.44-7.48 (m, 2H); MS [M-Br]$^+$: 481.

Example 143

Furan-2-ylmethyl-2-thiophen-2-ylmethylcarbamic acid 1-azabicyclo[2.2.2]oct-3-(R)yl ester The title compound was synthesised according to method a. The yield of the final step was 700 mg, 10%; $^1$H-NMR (DMSO-$d_6$): δ 1.10-1.34 (m, 1H), 1.44-1.67 (m, 3H), 1.93 (bs, 1H), 2.50-2.70 (m, 5H), 3.05-3.12 (m, 1H), 3.37-4.40 (m, 2H), 4.57-4.66 (m, 3H), 6.26-6.42 (m, 2H), 6.95-7.03 (m, 2H), 7.45 (m, 1H), 7.61 (m, 1H); MS [M+1]$^+$: 347.

Example 144

1-Allyl-3-(R)(furan-2-ylmethylthiophen-2-ylmethylcarbamoyloxy)-1-azoniabicyclo[2.2.2]octane; trifluoroacetate The title compound was synthesised according to method d. The yield of the final step was 7 mg, 15%; MS [M-CF$_3$COO]$^+$: 387.

Example 145

3-(R)(Furan-2-ylmethylthiophen-2-ylmethylcarbamoyloxy)-1-(3-phenylpropyl)-1-azoniabicyclo[2.2.2]octane; trifluoroacetate The title compound was synthesised according to method d. The yield of the final step was 11 mg, 20%; $^1$H-NMR (DMSO-$d_6$): δ 1.70-2.10 (m, 6H), 2.31 (bs, 1H), 2.59 (m, 2H), 3.15-3.50 (m, 7H), 3.84 (m, 1H), 4.36-4.56 (m, 4H), 5.03 (m, 1H), 6.32-6.44 (m, 2H), 6.92-7.08 (m, 2H), 7.20-7.35 (m, 5H), 7.41-7.46 (m, 1H), 7.59-7.62 m, 1H); MS [M-CF$_3$COO]$^+$: 465.

Example 146

3-(R)(bis-thiophen-2-ylmethylcarbamoyloxy)-1-(3-thiophen-2-ylpropyl)-1-azoniabicyclo[2.2.2]octane; bromide The title compound was synthesised according to method c. The yield of the final step was 690 mg, 81%; $^1$H-NMR (DMSO-$d_6$): δ 1.78-2.10 (m, 6H), 2.34 (bs, 1H), 2.82 (m, 2H), 3.21-3.46 (m, 7H), 3.89 (m, 1H), 4.54 (m, 4H), 5.06 (m, 1H), 6.95-7.01 (m, 4H), 7.07-7.11 (m, 2H), 7.38-7.49 (m, 3H); MS [M-Br]$^+$: 487; mp: 143° C.

Example 147

Allylthiophen-2-ylmethylcarbamic acid 1-azabicyclo[2.2.2]oct-3-(R)yl ester

The title compound was synthesised according to method a. The yield of the final step was 3220 mg, 30%; $^1$H-NMR (DMSO-$d_6$): δ 1.20-1.33 (m, 1H), 1.45-1.80 (m, 3H), 1.93 (bs, 1H), 2.49-2.72 (m, 5H), 3.05-3.09 (m, 1H), 3.81-3.83 (m, 2H), 3.83-4.55 (m, 3H), 5.14 (m, 2H), 5.70-5.82 (m, 1H), 6.96-7.04 (m, 2H), 7.44-7.45 (m, 1H); MS [M+1]$^+$: 307.

Example 148

1-Allyl-3-(R)(allylthiophen-2-ylmethylcarbamoyloxy)-1-azoniabicyclo[2.2.2]octane; trifluoroacetate The title compound was synthesised according to method d. The yield of the final step was 10 mg, 24%; $^1$H-NMR (DMSO-$d_6$): δ 1.80-2.10 (m, 4H), 2.32 (bs, 1H), 3.20-3.50 (m, 5H), 3.75-3.94 (m, 5H), 4.5-4.69 (m, 2H), 5.01 (m, 1H), 5.10-5.23 (m, 2H), 5.51-5.65 (m, 2H), 5.70-5.85 (m, 1H), 5.90-6.08 (m, 1H), 6.95-7.10 (m, 2H), 7.47 (m, 1H); MS [M-CF$_3$COO]$^+$: 347.

Example 149

3-(R)(Allylthiophen-2-ylmethylcarbamoyloxy)-1-(3-phenylpropyl)-1-azoniabicyclo[2.2.2]octane; trifluoroacetate The title compound was synthesised according to method d. The yield of the final step was 11 mg, 22%; $^1$H-NMR (DMSO-$d_6$): δ 1.74-2.10 m, 6H), 2.31 (bs, 1H), 2.59 (m, 2H), 3.16-3.56 (m, 7H), 3.76-3.90 (m, 3H), 4.48-4.71 (m, 2H), 4.99 (m, 1H), 5.11-5.23 (m, 2H), 5.72-5.83 (m, 1H), 6.98 (m, 1H), 7.06-7.07 (m, 1H), 7.20-7.35 (m, 5H), 7.44 (m, 1H); MS [M-CF$_3$COO]$^+$: 425.

Example 150

Cyclopentylthiophen-2-ylmethylcarbamic acid 1-azabicyclo[2.2.2]oct-3-(R)yl ester The title compound was synthesised according to method a. The yield of the final step was 2250 mg, 33%; $^1$H-NMR (DMSO-$d_6$): δ 1.20-1.40 (m, 1H), 1.45-1.72 (m, 11H), 1.89 (bs, 1H), 2.45-2.62 (m, 5H), 3.03-3.10 (m, 1H), 4.22 (bs, 1H), 4.50-4.56 (m, 3H), 6.93-6.99 (m, 2H), 7.38 (m, 1H); MS [M+1]$^+$: 335.

Example 151

1-Allyl-3-(R)(cyclopentylthiophen-2-ylmethylcarbamoyloxy)-1-azoniabicyclo[2.2.2]octane; trifluoroacetate The title compound was synthesised according to method d. The yield of the final step was 10 mg, 22%; $^1$H-NMR (DMSO-$d_6$): δ 1.40-2.05 (m, 12H), 2.27 (bs, 1H), 3.03, 3.42 (m, 5H), 3.70-3.95 (m, 3H), 4.15-4.35 (m, 1H), 5.58 (m, 2H), 4.99 (m, 1H), 5.54-5.65 (m, 2H), 5.87-6.10 (m, 1H), 6.97 (m, 1H), 7.03 (m, 1H), 7.41-7.43 (m, 1H); MS [M-CF$_3$COO]$^+$: 375.

Example 152

3-(R)(Cyclopentylthiophen-2-ylmethylcarbamoyloxy)-1-(3-phenylpropyl)-1-azoniabicyclo[2.2.2]octane; trifluoroacetate The title compound was synthesised according to method d. The yield of the final step was 13 mg, 24%; $^1$H-NMR (DMSO-$d_6$): δ 1.40-2.10 (m, 14H), 2.25 (bs, 1H), 2.58 (m, 2H), 2.95-3.50 (m, 7H), 3.81 (m, 1H), 4.26 (m, 1H), 4.50-4.70 (m, 2H), 4.97 (m, 1H), 6.93 (m, 1H), 7.03 (m, 1H), 7.20-7.40 (m, 6H); MS [M-CF$_3$COO]$^+$: 453.

Example 153

Furan-2-ylmethylphenylcarbamic acid 1-azabicyclo[2.2.2]oct-3-(R)yl ester

The title compound was synthesised according to method a. The yield of the final step was 1400 mg, 18%; $^1$H-NMR (DMSO-$d_6$): δ 1.19-1.60 (m, 4H), 1.84 (bs, 1H), 2.44-2.57 (m, 5H), 3.01-3.09 (m, 1H), 4.63 (m, 1H), 4.82 (s, 2H), 6.21 (m, 1H), 6.36 (m, 1H), 7.20-7.37 (m, 5H), 7.59 (m, 1H); MS [M+1]$^+$: 327.

Example 154

1-Allyl-3-(R)(furan-2-ylmethylphenylcarbamoyloxy)-1-azoniabicyclo[2.2.2]octane; trifluoroacetate The title compound was synthesised according to method d. The yield of the final step was 7 mg, 16%; $^1$H-NMR (DMSO-$d_6$): δ; MS [M-CF$_3$COO]$^+$: 367.

Example 155

3-(R)(Furan-2-ylmethylphenylcarbamoyloxy)-1-(3-phenylpropyl)-azoniabicyclo[2.2.2]octane; trifluoroacetate The title compound was synthesised according to method d. The yield of the final step was 11 mg, 21%; $^1$H-NMR (DMSO-$d_6$): δ 1.65-2.10 (m, 6H), 2.19 (bs, 1H), 2.59 (m, 2H), 3.10-3.50 (m, 7H), 3.83 (m, 1H), 4.85 (bs, 2H), 4.98 (m, 1H), 6.26 (m, 1H), 6.36 (m, 1H), 7.20-7.39 (m, 10H), 7.59 (m, 1H); MS [M-CF$_3$COO]$^+$: 445.

Example 156 bis-Furan-2-ylmethylcarbamic acid 1-azabicyclo[2.2.2]oct-3-(R)yl ester

The title compound was synthesised according to method a. The yield of the final step was 2100 mg, 22%; $^1$H-NMR (DMSO-$d_6$): δ 1.20-1.70 (m, 4H), 1.89 (bs, 1H), 2.45-2.71 (m, 5H), 3.00-3.12 (m, 1H), 4.40 (m, 4H), 4.62 (m, 1H), 6.22-6.40 (m, 4H), 7.59 (m, 2H); MS [M+1]$^+$: 331.

Example 157

1-Allyl-3-(R)(bis-furan-2-ylmethylcarbamoyloxy)-1-azoniabicyclo[2.2.2]octane; trifluoroacetate The title compound was synthesised according to method d. The yield of the final step was 7 mg, 16%; $^1$H-NMR (DMSO-$d_6$): δ; MS [M-CF$_3$COO]$^+$: 371.

Example 158

3-(R)(bis-furan-2-ylmethylcarbamoyloxy)-1-(3-phenylpropyl)-1-azoniabicyclo[2.2.2]octane; trifluoroacetate The title compound was synthesised according to method d. The yield of the final step was 11 mg, 20%; $^1$H-NMR (DMSO-$d_6$): δ 1.70-2.10 (m, 6H), 2.29 (bs, 1H), 2.59 (m, 2H), 3.10-3.50 (m, 7H), 3.82 (m, 1H), 4.32-4.54 (m, 4H), 5.01 (m, 1H), 6.29-6.41 (m, 4H), 7.20-7.35 (m, 5H), 7.57-7.61 (m, 2H); MS [M-CF$_3$COO]$^+$: 449.

Example 159

Benzylphenylcarbamic acid 1-azabicyclo[2.2.1]hept-4-yl ester

The title compound was synthesised according to method a. The yield of the final step was 4.86 mg, 1.3%, as formiate; $^1$H-NMR (DMSO-$d_6$): δ 1.86 (m, 4H), 2.65 (s, 2H), 2.77 (bs, 2H), 3.03 (bs, 2H), 4.84 (s, 2H), 7.14-7.32 (m, 10H), 8.19 (s, 1H); MS [M-HCOO]$^+$: 323.

Example 160

Benzylphenylcarbamic acid 1-azabicyclo[2.2.2]oct-4-yl ester

The title compound was synthesised according to method a. The yield of the final step was 2.56 mg, 1%, as formiate; $^1$H-NMR (DMSO-$d_6$): δ 1.81 (m, 6H), 2.83 (m, 6H), 4.81 (s, 2H), 7.14-7.32 (m, 10H), 8.24. (s, 1H); MS [M-HCOO]$^+$: 337

The examples 161 to 165 illustrate pharmaceutical compositions according to the present invention and procedures for their preparation.

Example 161

Preparation of a Pharmaceutical Composition: Tablets

Formulation:

| | |
|---|---|
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention was mixed with 340.8 g of lactose and 85.2 g of microcrystalline cellulose. The mixture was subjected to compression moulding using a roller compactor to give a flake-like compressed material. The flake-like compressed material was pulverized using a hammer mill, and the pulverized material was screened through a 20 mesh screen. A 4.5 g portion of light silicic anhydride and 4.5 g of magnesium stearate were added to the screened material and mixed. The mixer product was subjected to a tablets making machine equipped with a die/punch system of 7.5 mm in diameter, thereby obtaining 3,000 tablets each having 150 mg in weight.

Example 162

Preparation of a Pharmaceutical Composition: Tablets Coated

Formulation:

| Compound of the present invention | 5.0 mg |
| Lactose | 95.2 mg |
| Corn starch | 40.8 mg |
| Polyvinylpyrrolidone | 7.5 mg |
| Magnesium stearate | 1.5 mg |
| Hydroxypropylcellulose | 2.3 mg |
| Polyethylene glycol | 0.4 mg |
| Titanium dioxide | 1.1 mg |
| Purified talc | 0.7 mg |

Using a fluidized bed granulating machine, 15 g of the compound of the present invention was mixed with 285.6 g of lactose and 122.4 g of corn starch. Separately, 22.5 g of polyvinylpyrrolidone was dissolved in 127.5 g of water to prepare a binding solution. Using a fluidized bed granulating machine, the binding solution was sprayed on the above mixture to give granulates. A 4.5 g portion of magnesium stearate was added to the obtained granulates and mixed. The obtained mixture was subjected to a tablet making machine equipped with a die/punch biconcave system of 6.5 mm in diameter, thereby obtaining 3,000 tablets, each having 150 mg in weight. Separately, a coating solution was prepared by suspending 6.9 g of hydroxypropylmethylcellulose 2910, 1.2 g of polyethylene glycol 6000, 3.3 g of titanium dioxide and 2.1 g of purified talc in 72.6 g of water. Using a High Coated, the 3,000 tablets prepared above were coated with the coating solution to give film-coated tablets, each having 154.5 mg in weight.

Example 163

Preparation of a Pharmaceutical Composition: Liquid Inhalant

Formulation:

| Compound of the present invention | 400 µg |
| Physiological saline | 1 ml |

A 40 mg portion of the compound of the present invention was dissolved in 90 ml of physiological saline, and the solution was adjusted to a total volume of 100 ml with the same saline solution, dispensed in 1 ml portions into 1 ml capacity ampoule and then sterilized at 115° for 30 minutes to give liquid inhalant.

Example 164

Preparation of a Pharmaceutical Composition: Powder Inhalant

Formulation:

| Compound of the present invention | 200 µg |
| Lactose | 4,000 µg |

A 20 g portion of the compound of the present invention was uniformly mixed with 400 g of lactose, and a 200 mg portion of the mixture was packed in a powder inhaler for exclusive use to produce a powder inhalant.

Example 165

Preparation of a Pharmaceutical Composition: Inhalation Aerosol

Formulation:

| Compound of the present invention | 200 µg |
| Dehydrated (Absolute) ethyl alcohol USP | 8,400 µg |
| 1,1,1,2-Tetrafluoroethane (HFC-134A) | 46,810 µg |

The active ingredient concentrate is prepared by dissolving 0.0480 g of the compound of the present invention in 2.0160 g of ethyl alcohol. The concentrate is added to an appropriate filling apparatus. The active ingredient concentrate is dispensed into aerosol container, the headspace of the container is purged with Nitrogen or HFC-134A vapor (purging ingredients should not contain more than 1 ppm oxygen) and is sealed with valve. 11.2344 g of HFC-134A propellant is then pressure filled into the sealed container.

The invention claimed is:

1. A compound of formula (I):

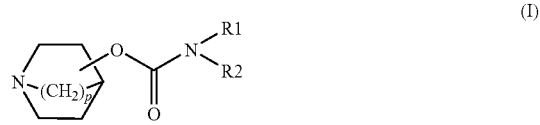

wherein
R1 represents

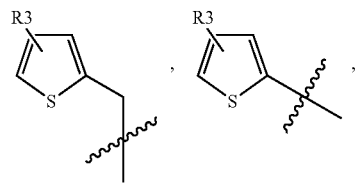

R3 represents a hydrogen or halogen atom, or a straight or branched lower alkyl group or a cyano group;

R2 represents a benzyl, phenethyl, furan-2-ylmethyl, furan-3-ylmethyl, thiophen-2-ylmethyl or thiophen-3-ylmethyl group or a straight or branched alkyl group having 3 to 8 carbon atoms, an alkenyl group having 3 to 8 carbon atoms, or a cycloalkyl group of 3 to 6 carbon atoms;

p is 2 and the substitution in the azoniabicyclic ring may be in the 2, 3 or 4 position including all possible configurations of the asymmetric carbons;

or a mixture thereof;

or a pharmaceutically acceptable salt thereof.

2. A compound according to claim 1, wherein said compound is a quaternary ammonium salt of a carbamate of formula (I), wherein said compound is represented by formula (II):

$$B-(CH_2)_n-A-(CH_2)_m-N^+(CH_2)_p-O-C(=O)-N(R1)(R2) \quad X^-$$ (II)

wherein m is an integer from 0 to 8;

A represents a —CH$_2$—, —CH=CR4-, —CR4=CH—, —CO—, —O—, —S—, —S(O), —SO$_2$—, —NR4-, or —CR4R5- group, wherein R4 and R5 each independently represent a hydrogen atom, a straight or branched lower alkyl group, or R4 and R5 together form an alicyclic ring;

n is an integer from 0 to 4;

B represents a hydrogen atom, an alkoxy group, a cycloalkyl group, —COOR4 or —OOCR4, or a cyano group, a naphthalenyl group, a 5,6,7,8-tetrahydronaphthalenyl group, a biphenyl group, or a group of formula (I) or (ii)

(i) [heterocyclic ring with Z and R3]

(ii) [phenyl ring with R6, R7, R8]

wherein Z represents O, N or S; and

R6, R7 and R8 each independently represent a hydrogen or halogen atom, or a hydroxyl, phenyl, —OR4, —SR4, —NR4R5, —NHCOR4, —CONR4R5, —CN, —NO$_2$, —COOR4 or —CF$_3$ group or a straight or branched, substituted or unsubstituted lower alkyl group;

wherein R4 and R5 each independently represent a hydrogen atom, a straight or branched lower alkyl group, or R4 and R5 together form an alicyclic ring; or R6 and R7 together form an aromatic, alicyclic or heterocyclic ring; and X represents a pharmaceutically acceptable anion of a mono or polyvalent acid or a mixture thereof of compounds of formula (II).

3. A compound according to claim 1, wherein R1 represents a thiophen-2-ylmethyl, thienyl or furan-2-ylmethyl group.

4. A compound according to claim 1, wherein R2 represents a benzyl, thiophen-2-ylmethyl, thiophen-3-ylmethyl, furan-2-ylmethyl, phenethyl, pent-4-enyl, pentyl, butyl, allyl or cyclopentyl group.

5. A compound according to claim 2, wherein B represents a hydrogen atom or a substituted or unsubstituted phenyl, pyrrolyl, thienyl or furyl group, or a biphenyl, naphthalenyl, 5,6,7,8-tetrahydronaphthalenyl or benzo[1,3]dioxolyl group.

6. A compound according to claim 5, wherein B represents a substituted or unsubstituted phenyl group and R6, R7 and R8 each independently represent a hydrogen or halogen atom, or a hydroxyl, methyl, —CH$_2$OH, —OMe, —NMe$_2$, —NHCOMe, —CONH$_2$, —CN, —NO2, —COOMe, or —CF$_3$ group.

7. A compound according to claim 6, wherein B represents a phenyl, 4-fluorophenyl or 3-hydroxyphenyl group.

8. A compound according to claim 2, wherein n=0 or 1; m is an integer from 1 to 6; and A represents a —CH$_2$—, —CH=CH—, —CO—, —NMe-, —O— or —S— group.

9. A compound according to claim 8, wherein m is 1, 2 or 3 and A represents a —CH2-, —CH=CH—, or —O— group.

10. A compound according to claim 2, wherein B—(CH$_2$)$_n$-A-(CH$_2$)$_m$— represents a group selected from 3-phenoxypropyl, 2-phenoxyethyl, 3-phenylallyl, phenethyl, 3-phenylpropyl, 3-(3-hydroxyphenoxy)propyl, 3-(4-fluorophenoxy)propyl, 3-thiophen-2-ylpropyl, 1-allyl and 1-heptyl.

11. A compound according to claim 2, wherein X⁻ represents a chloride, bromide, or trifluoroacetate anion.

12. A compound according to claim 1, wherein the azoniabicyclo group is substituted in the 3-position.

13. A compound according to claim 1, wherein the azoniabicyclo group is substituted in the 3'-position and the substituent at the 3-position has the (R) configuration.

14. A compound according to claim 1, which is a single isomer.

15. A compound according to claim 1 which is:
Butylthiophen-2-ylmethylcarbamic acid 1-azabicyclo[2.2.2]oct-3-(R)yl ester
Bis-thiophen-2-ylmethylcarbamic acid 1-azabicyclo[2.2.2]oct-3-(R)-yl ester
Furan-2-ylmethyl-2-ylmethylcarbamic acid 1-azabicyclo[2.2.2]oct-3-(R)yl ester
Allylthiophen-2-ylmethylcarbamic acid 1-azabicyclo[2.2.2]oct-3-(R)yl ester
Cyclopentylthiophen-2-ylmethylcarbamic acid 1-azabicyclo[2.2.2]oct-3-(R)yl ester
Bis-furan-2-ylmethylcarbamic acid 1-azabicyclo[2.2.2]oct-3-(R)yl ester
or a pharmaceutically acceptably salt thereof.

16. A compound according to claim 2 which is:
3-(R)(Bis-thiophen-2-ylmethylcarbamoyloxy)-1-(3-phenylpropyl)-1-azoniabicyclo[2.2.2]octane; bromide
3-(R)(Bis-thiophen-2-ylmethylcarbamoyloxy)-1-(3-thiophen-2-ylpropyl)-1-azoniabicyclo[2.2.2]octane; bromide
1-Allyl-3-(R)(allylthiophen-2-ylmethylcarbamoyloxy)-1-azoniabicyclo[2.2.2]octane; trifluoroacetate
3-(R)(Cyclopentylthiophen-2-ylmethylcarbamoyloxy)-1-(3-phenylpropyl)-1-azoniabicycle[2.2.2]octane; trifluoroacetateor
1-Allyl-3-(R)(bis-furan-2-ylmethylcarbamoyloxy)-1-azoniabicyclo[2.2.2]octane; trifluoroacetate.

17. A compound according to claim 1 characterised in that it has an IC$_{50}$ value (nM) for muscarinic M3 receptors of less than 35.

18. A process for the preparation of a compound of formula (I) as claimed in claim 1,

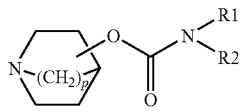

(I)

which process comprises reacting a compound of formula (III):

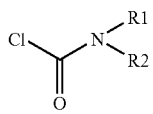

(III)

with a compound of formula (IV):

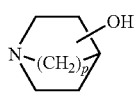

(IV)

and optionally preparing a pharmaceutically acceptable salt of a compound of formula (I).

19. A process for producing a salt of formula (II) as claimed in claim 2:

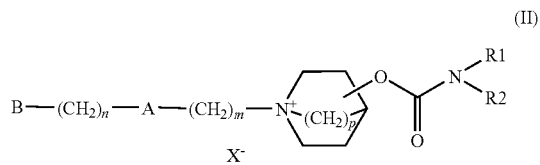

(II)

which process comprises quaternising the nitrogen atom of the azoniabicyclic ring of a compound of formula (I):

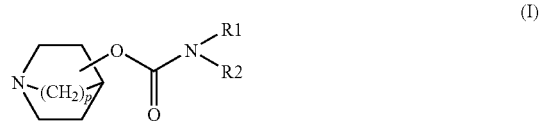

(I)

with an alkylating agent of formula (VI):

(VI)

B—CH$_2$)$_n$-A-(CH$_2$)$_m$—W wherein W represents a leaving group.

20. A process according to claim 19, wherein W represents a group X.

21. A process according to claim 19, wherein the resulting reaction mixture is purified by solid phase extraction.

22. A pharmaceutical composition comprising a compound according to claim 1 and a pharmaceutically acceptable carrier or diluent.

23. A compound according to claim 2, wherein R1 represents a thiophen-2-ylmethyl, thienyl or furan-2-ylmethyl group.

24. A compound according to claim 2, wherein R2 represents a benzyl, thiophen-2-ylmethyl, thiophen-3-ylmethyl, furan-2-ylmethyl, phenethyl, pent-4-enyl, pentyl, butyl, allyl or cyclopentyl group.

25. A compound according to claim 2, wherein the azoniabicyclo group is substituted in the 3-position.

26. A compound according to claim 25, wherein the substituent at the 3-position has the (R) configuration.

27. A compound according to claim 2, which is a single isomer.

28. A compound according to claim 2 characterised in that it has an IC$_{50}$ value (nM) for muscarinic M3 receptors of less than 35.

29. A pharmaceutical composition comprising a compound according to claim 2 and a pharmaceutically acceptable carrier or diluent.

* * * * *